US006410317B1

(12) United States Patent
Farmer

(10) Patent No.: US 6,410,317 B1
(45) Date of Patent: Jun. 25, 2002

(54) RECOMBINASE-BASED METHODS FOR PRODUCING EXPRESSION VECTORS AND COMPOSITIONS FOR USE IN PRACTICING THE SAME

(75) Inventor: Andrew Alan Farmer, Mountain View, CA (US)

(73) Assignee: Clontech Laboratories, Inc., Palo Alto, CA (US)

(*) Notice: Subject to any disclaimer, the term of this patent is extended or adjusted under 35 U.S.C. 154(b) by 115 days.

(21) Appl. No.: 09/616,651

(22) Filed: Jul. 14, 2000

Related U.S. Application Data

(63) Continuation-in-part of application No. 09/356,001, filed on Jul. 14, 1999, now abandoned.

(51) Int. Cl.$^7$ .............................................. C12N 15/63
(52) U.S. Cl. .................................................. 435/320.1
(58) Field of Search ...................................... 435/320.1

(56) References Cited

U.S. PATENT DOCUMENTS

| | | |
|---|---|---|
| 4,959,317 A | 9/1990 | Sauer |
| 5,378,618 A | 1/1995 | Sternberg et al. |
| 5,527,695 A | 6/1996 | Hodges et al. |
| 5,851,808 A | 12/1998 | Elledge et al. |
| 5,888,732 A | 3/1999 | Hartley et al. |

FOREIGN PATENT DOCUMENTS

| | | |
|---|---|---|
| EP | 0 559 725 B1 | 11/1991 |
| WO | WO 91 02801 | 3/1991 |
| WO | WO 93 15191 | 8/1993 |
| WO | WO 94 09127 | 4/1994 |
| WO | WO 96/30498 | 3/1996 |
| WO | WO 00/05355 | 7/1998 |
| WO | WO 00/12687 | 3/2000 |

OTHER PUBLICATIONS

Baubonis et al.(1993), "Genomic Targeting with Purified Cre Recombinase," *Nucleic Acids Research*, vol. 21(9): 2025–2029.

Bayley et al. (1992), "Exchange of Gene Activity in Transgenic Plants Catalyzed by the Cre–lox Site–Specific Recombination System," *Plant Molecular Biology*, vol. 18: 353–361.

Bevan, Michael (1984), "Binary Agrobacterium Vectors for Plants Transformation," *Nucleic Acids Research*, vol. 12 No. 22.

Fukushige et al. (1992), "Genomic Targeting with a Positive–Selection Lox Integration Vector Allows Highly Reproducible Gene Expression in Mammalian Cells," *Proc. Natl. Acad. Sci. USA*, vol. 89 pp. 7905–7909.

Liu et al. (1998), "The Univector Plasmid–Fusion System, A Method for Rapid Construction of Recombinant DNA without Restriction Enzymes," *Current Biology*, vol. 8: 1300–1309.

Pósfai et al. (1994), "In Vivo Excision and Amplification of Large Segments of the Escherichia Colo Genome," *Nucleic Acids Research*, vol. 22 (12): 2392–2398.

Qin et al. (1994), "Cre Recombinase–Mediated Site–Specific Recombination Between Plant Chromosomes," *Proc. Natl. Acad. Sci. USA*, vol. 81: 1706–1710.

Sauer et al. (1989), "Cre–Stimulated Recombination at loxP–Containing DNA Sequences Placed into the Mammalian Genome," *Nucleic Acids Research*, vol. 17 (1): 147–161.

Sauer et al. (1987), "Site–Specific Insertion of DNA into a Pseudorabies Virus Vector," *Proc. Natl. Acad. Sci. USA*, vol. 84: 9108–9112.

Sauer et al. (1992), "Construction of Isogenic Cell Lines Expressing Human and Rat Angiotensin II AT1 Receptors by Cre–Mediated Site Specific Recombination," *METHODS: A Companion to Methods in Enzymology*, vol. 4: 143–149.

Sauer et al. (1990), "Targeted Insertion of Exogenous DNA into the Eukaryotic Genome by the Cre Recombinase," *The New Biologist*, vol. 2 (5) : 441–449.

Ronald Hoess et al. "Formation of small circular DNA molecules via an vitro site–specific recombination system" *Gene* 4 (1985) 325–329.

Cydne L. Holt et al. "A novel phage λreplacement Cre–1ox vector that has automatic subcloning capabilities" *Gene* 133 (1993) 95–97.

*Primary Examiner*—Terry McKelvey
(74) *Attorney, Agent, or Firm*—Bret E. Field; Bozicevic, Field & Francis; Kathleen Dal Bon

(57) ABSTRACT

Methods are provided for producing an expression vector. In the subject methods, donor and acceptor vectors are combined in the presence of a recombinase to produce an expression vector that includes a first and second recombinase recognition site oriented in the same direction, wherein the first and second recombination sites are able to recombine with each other. In the subject methods, one of the donor and acceptor vectors includes a single recombinase recognition site while the other includes two recombinase recognition sites. Also provided are compositions for use in practicing the subject methods, including the donor and acceptor vectors themselves, as well as systems and kits that include the same. The subject invention finds use in a variety of different applications, including the transfer or cloning of a nucleic acid of interest from a first vector into one or more expression vectors, etc.

28 Claims, 16 Drawing Sheets

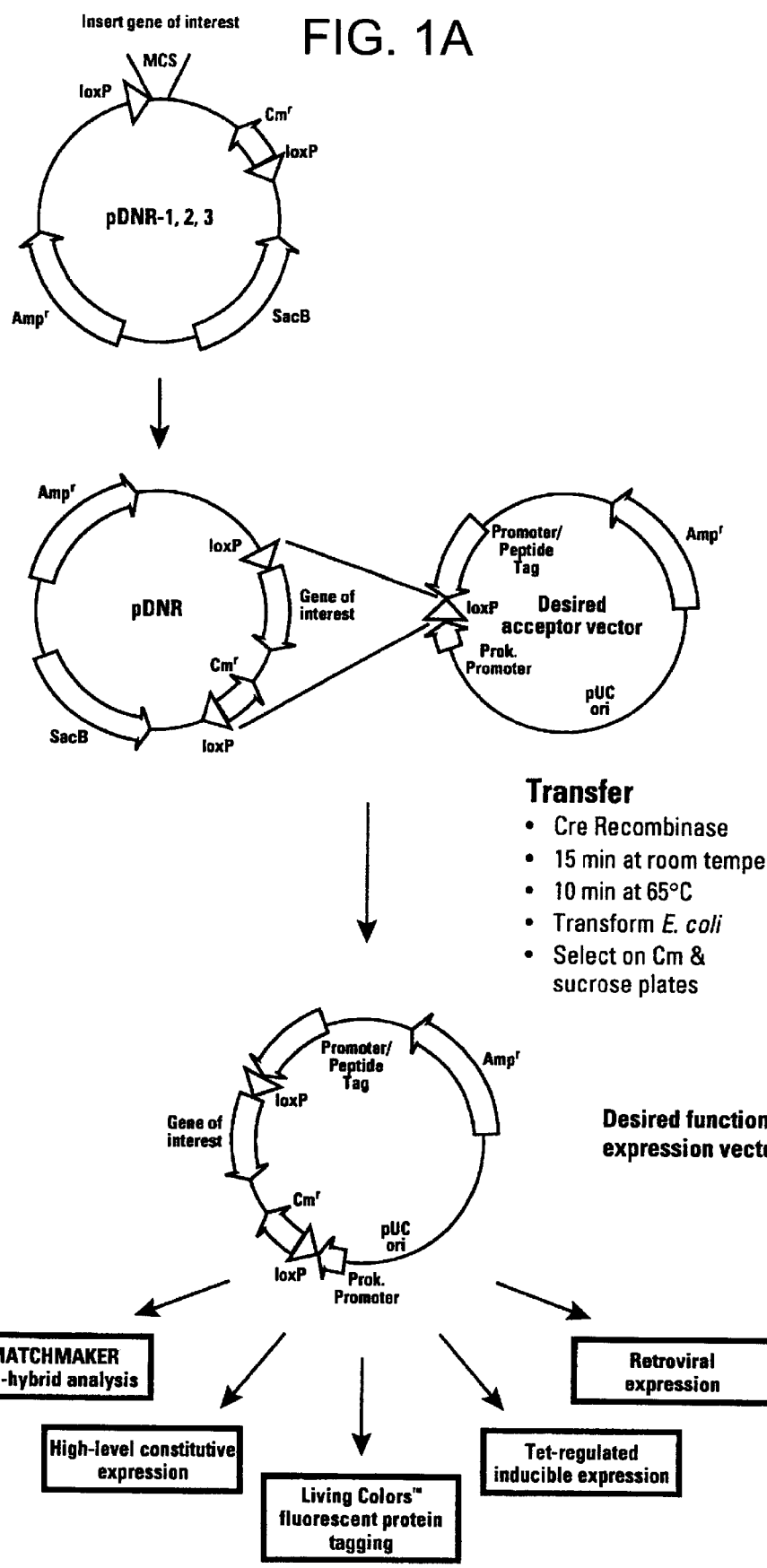

FIG. 1B pDNR-1 (reading frame 1):

```
loxP      45
         •
TTA TCA GTC GAC GGT ACC GGA CAT ATG CCC GGG AAT TCC TGC AGG ATC CGC TCG AG
        Sal I   Kpn I    Nde I  Sma I  EcoR I  Pst I BamH I    Xho I
```

```
     95                                          STOPs
      •                                        ⌒
     A AGC TTT CTA GAC CAT TCG TTT GGC GCG CGG GCC CAG TAG GTA AGT GAA  (SEQ ID NO. 19)
       Hind III  Xba I     BstX I         BssH II  Bsp120 I
                                                   Apa I
``` pDNR-2 (reading frame 2):

```
loxP      45
         •
TTA TCA GTC GAC TGG TAC CAG ACA TAT GCC CGG GAA TTC CTG CAG GAT CCG CTC GAG
        Sal I    Kpn I    Nde I  Sma I  EcoR I  Pst I  BamH I    Xho I
```

```
     94                                          STOPs
      •                                        ⌒
     AAG CTT TCT AGA CCA TTC GTT TGG CGC GCA TGC A GTA GGT AAG TGA  (SEQ ID NO. 20)
     Hind III  Xba I    BstX I      BssH II  Sph I
                                    BssH II
``` pDNR-3 (reading frame 3):

```
loxP      45
         •
TTA TCA GTC GAC TCG GTA CCG AGC ATA TGC CCG GGA ATT CCT GCA GGA TCC GCT CGA
        Sal I    Kpn I    Nde I  Sma I  EcoR I  Pst I  BamH I    Xho I
```

```
     94                                          STOPs
      •                                        ⌒
     AA GCT TAT CTA GAC ATT CGT TTG GCG CGC ATG CAT AGT AGG TAA  (SEQ ID NO. 21)
     Hind III  Xba I             BssH II    Nsi I
```

RECOMBINASE-BASED METHODS FOR PRODUCING EXPRESSION VECTORS AND COMPOSITIONS FOR USE IN PRACTICING THE SAME

CROSS-REFERENCE TO RELATED APPLICATIONS

This application is a continuation-in-part of application Ser. No. 09/356,001 filed on Jul. 14, 1999, now abandoned; the disclosure of which is herein incorporated by reference.

INTRODUCTION

1. Field of the Invention

The field of this invention is molecular biology, particularly recombinant DNA engineering.

2. Background of the Invention

The processes of isolating, cloning and expressing genes are central to the field of molecular biology and play prominent roles in research and industry in biotechnology and related fields. Until recently, the isolation and cloning of genes has been achieved in vitro using restriction endonucleases and DNA ligases. Restriction endonucleases are enzymes which recognize and cleave double-stranded DNA at a specific nucleotide sequence, and DNA ligases are enzymes which join fragments of DNA together via the phosphodiester bond. A DNA sequence of interest can be "cut" or digested into manageable pieces using a restriction endonuclease and then inserted into an appropriate vector for cloning using DNA ligase. However, in order to transfer the DNA of interest into a different vector—most often a specialized expression vector—restriction enzymes must be used again to excise the DNA of interest from the cloning vector, and then DNA ligase is used again to ligate the DNA of interest into the chosen expression vector.

The ability to transfer a DNA of interest to an appropriate expression vector is often limited by the availability or suitability of restriction enzyme recognition sites. Often multiple restriction enzymes must be employed to remove the desired coding region. Further, the reaction conditions used for each enzyme may differ such that it is necessary to perform the excision reaction in separate steps, or it may be necessary to remove a particular enzyme used in an initial restriction enzyme reaction prior to completing subsequent restriction enzyme digestions due to buffer and/or cofactor incompatibility. Many of these extra steps require time-consuming purification of the subcloning intermediate.

There is, therefore, a need to develop protocols and compositions for the rapid transfer of a DNA molecule of interest from one vector to another in vitro or in vivo without the need to rely upon restriction enzyme digestions.
Relevant Literature U.S. Patents of interest include: U.S. Pat. Nos. 5,527,695; 5,744,336; 5,851,808; 5,888,732; and 5,962,255. Also of interest is Liu et al., Current Biology (1998) 8:1300–1309.

SUMMARY OF THE INVENTION

Methods are provided for producing an expression vector. In the subject methods, donor and acceptor vectors are combined in the presence of a recombinase to produce an expression vector that includes a first and second recombinase recognition site oriented in the same direction, wherein said first and said second recombinase recognition sites are capable of recombining with each other. In the subject methods, one of the donor and acceptor vectors includes a single recombinase recognition site while the other includes two recombinase recognition sites. Also provided are compositions for use in practicing the subject methods, including the donor and acceptor vectors themselves, as well as systems and kits that include the same. The subject invention finds use in a variety of different applications.

BRIEF DESCRIPTION OF THE FIGURES

FIGS. 1A–1B. FIG. 1A provides a schematic representation of a preferred embodiment of the subject methods. FIG. 1B provides the reading frames pDNR-1 to pDNR-3 vectors depicted in FIGS. 2A to 2C, respectively.

FIGS. 3A to 3J provide schematic representations of 15 different acceptor plasmids, i.e., pLP-GADT7; pLP-GBKT7; pLP-EGFP-C1; pLP-ECFP-C1; pLP-EYFP-C1; pLP-IRESneo; pLP-IRES2-EGFP; pLP-TRE2; pLP-RevTRE; and pLP-LNCX suitable for use with the donor plasmids pDNR-1; pDNR-2 and pDNR-3. Other specific acceptor vectors of interest are pLP-ProTet; pLP-CMV-Myc; pLP-CMV-HA; pLP-Shuttle; pLP-AdenoX, as described more fully in the specification.

DEFINITIONS

Figure 2A:
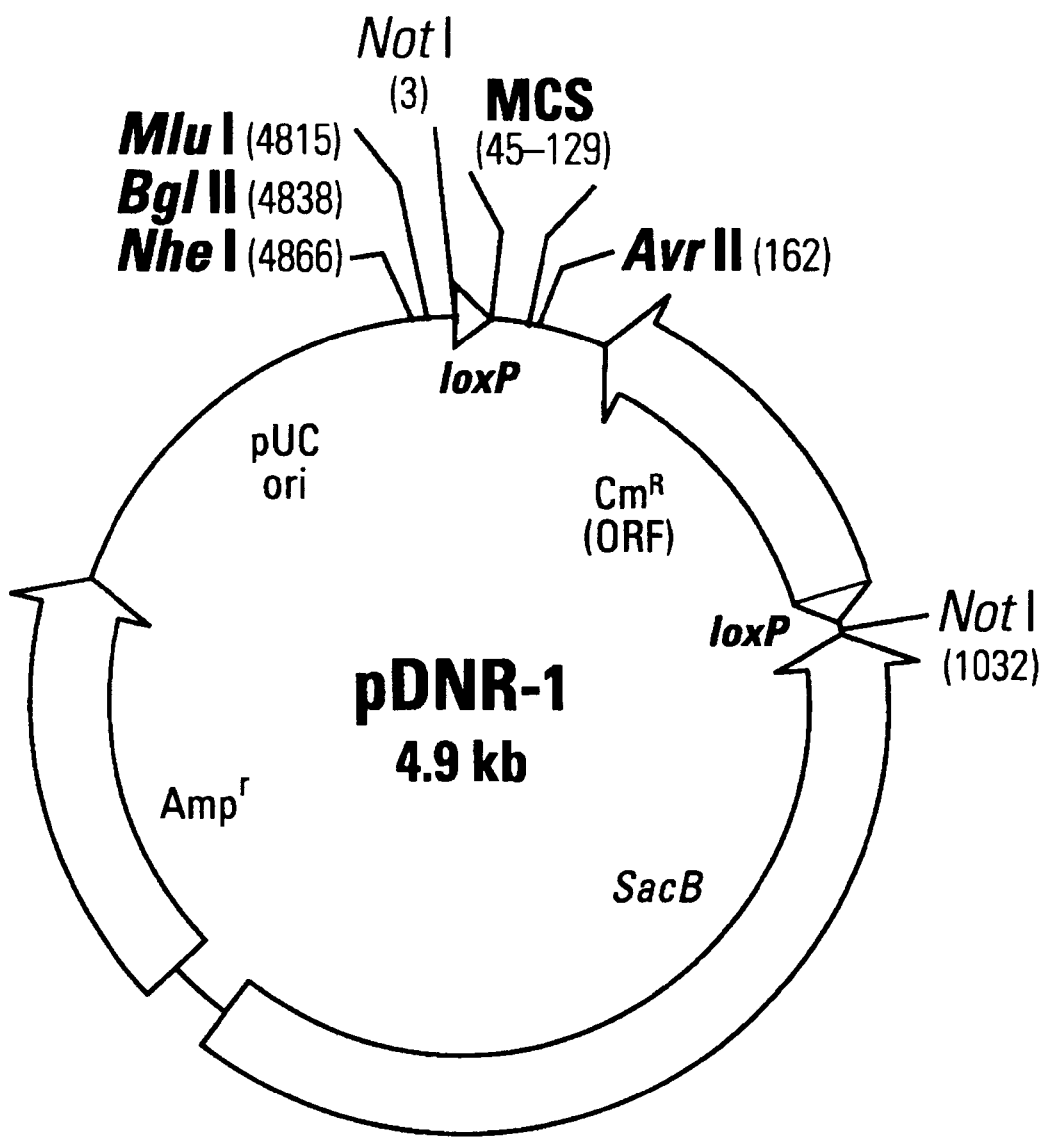
FIGS. 2A to 2D provide schematic representations of four different donor plasmid vectors, i.e., pDNR-1; pDNR-2; and pDNR-3; pDNR-Lib according to a preferred embodiment of the subject invention.

As used herein, the term "donor construct" refers to a donor vector, i.e., a donor nucleic acid construct comprising two donor sequence-specific recombinase target sites each having a defined 5' to 3' orientation and placed in the donor construct such that they have the same 5' to 3' orientation, and a unique restriction enzyme site or polylinker, wherein the restriction enzyme site or polylinker is located 3' of the first-donor sequence-specific recombinase target site and 5' of the second-donor sequence-specific recombinase target site, and wherein the recombinase recognition sites are capable of recombining with each other.

As used herein, the term "first donor fragment" or "desired donor fragment" refers to the fragment produced when the donor construct is resolved, comprising a single sequence-specific recombinase target site having a 5' to 3' orientation wherein the 5' half of the single sequence-specific recombinase target site is derived from the 5' half of the second-donor sequence-specific recombinase target site in the donor construct and the 3' half of the single sequence-specific recombinase target site is derived from the 3' half of the first-donor sequence-specific recombinase target site of the donor construct, a polylinker or unique restriction site 3' to said sequence-specific recombinase target site, and the donor-partial selectable marker, or in certain embodiments, a donor-functional selectable marker. It is the first donor fragment that will combine with the acceptor construct to produce the final desired recombination product.

As used herein the term "second donor fragment" or "non-desired donor fragment" refers to the fragment produced when the donor construct is resolved, comprising a single sequence-specific recombination target site in which the 5' half is derived from the 5' half of the first-donor sequence-specific recombinase target site from the donor construct and the 3' half is derived from the 3' half of the second-donor sequence-specific recombinase target site from the donor construct.

As used herein, the term "acceptor construct" refers to an acceptor nucleic acid construct comprising at least one origin of replication, an acceptor sequence-specific recombinase target site having a defined 5' to 3' orientation, a first promoter located at the 5' end of the acceptor sequence-specific recombinase target site, and in certain embodiments, an acceptor-partial selectable marker.

As used herein, "final recombination constructs" refers to the recombination products produced when either the first donor fragment or the second donor fragment recombines with an acceptor construct, i.e., to generate expression vectors produced by the subject methods.

As used herein, "final desired recombination construct" refers to a recombination product produced when the first, or desired, donor fragment recombines with an acceptor construct, i.e., an expression construct.

The terms "sequence-specific recombinase" and "site-specific recombinase" refer to enzymes or recombinases that recognize and bind to a short nucleic acid site or "sequence-specific recombinase target site", i.e., a recombinase recognition site, and catalyze the recombination of nucleic acid in relation to these sites. These enzymes include recombinases, transposases and integrases.

The terms "sequence-specific recombinase target site", "site-specific recombinase target site", "sequence-specific target site" and "site-specific target site" refer to short nucleic acid sites or sequences, i.e., recombinase recognition sites, which are recognized by a sequence- or site-specific recombinase and which become the crossover regions during a site-specific recombination event. Examples of sequence-specific recombinase target sites include, but are not limited to, lox sites, att sites, dif sites and frt sites.

The term "lox site" as used herein refers to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, loxΔ86, loxΔ117, loxC2, loxP2, loxP3 and lox P23.

The term "frt site" as used herein refers to a nucleotide sequence at which the product of the FLP gene of the yeast 2 micron plasmid, FLP recombinase, can catalyze site-specific recombination.

The term "unique restriction enzyme site" indicates that the recognition sequence of a given restriction enzyme appears once within a nucleic acid molecule.

A restriction enzyme site or restriction site is said to be located "adjacent to the 3' end of a sequence-specific recombinase target site" if the restriction enzyme recognition site is located downstream of the 3' end of the sequence-specific recombinase target site. The adjacent restriction enzyme site may, but need not, be contiguous with the last or 3' most nucleotide comprising the sequence-specific recombinase target site.

The terms "polylinker" or "multiple cloning site" refer to a cluster of restriction enzyme sites, typically unique sites, on a nucleic acid construct that can be utilized for the insertion and/or excision of nucleic acid sequences, such as the coding region of a gene, loxP sites, etc.

The term "termination sequence" refers to a nucleic acid sequence which is recognized by the polymerase of a host cell and results in the termination of transcription. Prokaryotic termination sequences commonly comprise a GC-rich region that has a two-fold symmetry followed by an AT-rich sequence. A commonly used termination sequence is the T7 termination sequence. A variety of termination sequences are known in the art and may be employed in the nucleic acid constructs of the present invention, including the TINT3, TL13, TL2, TR1, TR2, and T6S termination signals derived from the bacteriophage lambda, and termination signals derived from bacterial genes, such as the tip gene of E. coli.

The terms "polyadenylation sequence" (also referred to as a "poly $A^+$ site" or "poly $A^+$ sequence") as used herein denotes a DNA sequence which directs both the termination and polyadenylation of the nascent RNA transcript. Efficient polyadenylation of the recombinant transcript is desirable, as transcripts lacking a poly $A^+$ tail are typically unstable and rapidly degraded. The poly $A^+$ signal utilized in an expression vector may be "heterologous" or "endogenous". An endogenous poly $A^+$ signal is one that is found naturally at the 3' end of the coding region of a given gene in the genome. A heterologous poly $A^+$ signal is one which is isolated from one gene and placed 3' of another gene, e.g., coding sequence for a protein. A commonly used heterologous poly $A^+$ signal is the SV40 poly $A^+$ signal. The SV40 poly $A^+$ signal is contained on a 237 bp BamHI/BclI restriction fragment and directs both termination and polyadenylation; numerous vectors contain the SV40 poly $A^+$ signal. Another commonly used heterologous poly $A^+$ signal is derived from the bovine growth hormone (BGH) gene; the BGH poly $A^+$ signal is also available on a number of commercially available vectors. The poly $A^+$ signal from the Herpes simplex virus thymidine kinase (HSV tk) gene is also used as a poly $A^+$ signal on a number of commercial expression vectors.

As used herein, the terms "selectable marker" or "selectable marker gene" refer to a gene which encodes an enzymatic activity and confers the ability to grow in medium lacking what would otherwise be an essential nutrient; in addition, a selectable marker may confer upon the cell in which the selectable marker is expressed, resistance to an antibiotic or drug. A selectable marker may be used to confer a particular phenotype upon a host cell. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene; selectable markers used in this manner are referred to as negative selectable markers.

As used herein, the term "donor-partial selectable marker" found in certain embodiments of the subject invention refers to portion of a selectable marker gene encoded by the donor construct which is non-functional by itself, by which is meant that it must be positioned on a vector in operable relation with another element in order to be expressed. Examples of donor-partial selectable markers are coding sequences and promoter regions of complete selectable markers of functioning expression modules or cassettes.

As used herein, the term "donor-functional selectable marker" found in certain embodiments of the subject invention refers to a functional selectable marker gene encoded by the donor construct.

As used herein, the term "acceptor-partial selectable marker" found in certain embodiments of the subject invention refers to a portion of a selectable marker gene encoded by the acceptor construct which is non-functional by itself, as described above, e.g., a coding sequence or promoter by itself As used herein, the term "acceptor-functional selectable marker" found in certain embodiments of the subject invention refers to a functional selectable marker gene encoded by the acceptor construct.

As used herein, the term "recombinant-functional selectable marker" refers to the functional selectable marker gene created upon recombination between the donor construct and the acceptor construct which results in the adjacent placement of the donor-partial selectable marker and the acceptor-partial selectable marker, i.e., flanking either side of a recombinase site.

As used herein, the term "construct" is used in reference to nucleic acid molecules that transfer DNA segment(s) from one cell to another. The term "vector" is sometimes used interchangeably with "construct". The term "construct" includes circular nucleic acid constructs such as plasmid constructs, phagemid constructs, cosmid vectors, etc., as well as linear nucleic acid constructs including, but not limited to, PCR products. The nucleic acid construct may comprise expression signals such as a promoter and/or an enhancer in operable linkage, and then is generally referred to as an "expression vector" or "expression construct".

The term "expression construct" as used herein refers to an expression module or expression cassette made up of a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that the reading frame is maintained and a functional protein is produced.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

Transformation of prokaryotic cells may be accomplished by a variety of means known in the art, including the treatment of host cells with $CaCl_2$ to make competent cells, electroporation, etc. Transfection of eukaryotic cells may be accomplished by a variety of means known in the art, including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "host" is meant to include not only prokaryotes, but also eukaryotes, such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Saccharomyces cerevisiae, Schizosaccharomyces pombe, Pichia pastoris*, mammalian cells and insect cells, and, plant cells, such as *Arabidopsis thaliana* and *Tobaccum nicotiana*.

As used herein, the terms "restriction endonucleases" and "restriction enzymes" refer to bacterial enzymes, each of which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule". The term "recombinant protein" or "recombinant polypeptide" as used herein refers to a protein molecule which is expressed from a recombinant DNA molecule.

The ribose sugar is a polar molecule, and therefore, DNA is referred to as having a 5' to 3', or 5' to 3', directionality. DNA is said to have "5' ends" and "3' ends" because mononucleotides are reacted to make oligonucleotides in a manner such that the 5' phosphate of one mononucleotide pentose ring is attached to the 3' oxygen of its neighbor via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also has a 5' to 3' orientation. In either a linear or circular DNA molecule, discrete elements are referred to as being "upstream" or "5'" of the "downstream" or "3'" elements. This terminology reflects the fact that DNA has an inherent 5' to 3' polarity, and transcription typically proceeds in a 5' to 3' fashion along the DNA strand. The promoter and enhancer elements which direct transcription of an operably linked coding region, or open reading frame, are generally located 5', or upstream, of the coding region. However, enhancer elements can exert their effect even when located 3' of the promoter and coding region. Transcription termination and polyadenylation signals are typically located 3' or downstream of the coding region.

The 3' end of a promoter is said to be located upstream of the 5' end of a sequence-specific recombinase target site when, moving in a 5' to 3' direction along the nucleic acid molecule, the 3' terminus of a promoter precedes the 5' end of the sequence-specific recombinase target site. When the acceptor construct is intended to permit the expression of a translation fusion, the 3' end of the promoter is located upstream of both the sequences encoding the amino-terminus of a fusion protein and the 5' end of the sequence-specific recombinase target site. Thus, the sequence-specific recombinase target site is located within the coding region of the fusion protein (i.e., located downstream of both the promoter and the sequences encoding the affinity domain, such as Gst).

As used herein, the term "adjacent", in the context of positioning of genetic elements in the constructs, shall mean within about 0 to 2500, sometimes 0 to 1000 bp and sometimes within about 0 to 500, 0 to 400, 0 to 300 or 0 to 200 bp.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with proteins that can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence includes, at its 3' terminus, the transcription initiation site and extends upstream (in the 5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length.

As used herein, "an origin of replication" or "origin" refers to any sequence capable of directing replication of a DNA construct in a suitable prokaryotic or eukaryotic host (e.g., the ColE1 origin and its derivatives; the yeast $2\mu$ origin). Eukaryotic expression vectors may also contain "viral replicons" or "origins of replication". Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene, i.e., the coding sequence for a protein or polypeptide of interest, including sequences located adjacent to the coding region on both the 5' and 3' ends for a distance of about 1 kb on either end, such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene which are transcribed into heteronuclear RNA (hnRNA); introns may contain regulatory elements such as enhancers. Introns are removed or "spliced out" from the nuclear or primary transcript; introns therefore are absent in the mature messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "purified" or "to purify" refers to the removal of contaminants from a sample. For example, recombinant Cre polypeptides are expressed in bacterial host cells (e.g., as a GST-Cre or $(HN)_6$-Cre fusion protein) and the Cre polypeptides are purified by the removal of host cell proteins; the percent of recombinant Cre polypeptides is thereby enriched or increased in the sample.

As used herein the term "portion" refers to a fraction of a sequence, gene or protein. "Portion" may comprise a fraction greater than half of the sequence, gene or protein, equal to half of the sequence, gene or protein or less than half of the sequence, gene or protein. Typically as used herein, two or more "portions" combine to comprise a whole sequence, gene or protein.

As used herein, the term "fusion protein" refers to a chimeric protein containing a protein of interest joined to an exogenous protein fragment. The fusion partner may enhance solubility of the protein of interest as expressed in a host cell, may provide an affinity tag to allow purification of the recombinant fusion protein from the host cell or culture supernatant, or both. If desired, the fusion protein may be removed from the protein of interest by a variety of enzymatic or chemical means known to the art.

DESCRIPTION OF THE SPECIFIC EMBODIMENTS

Methods are provided for producing an expression vector. In the subject methods, donor and acceptor vectors are combined in the presence of a recombinase to produce an expression vector that includes a first and second recombinase recognition site oriented in the same direction. . In the subject methods, one of the donor and acceptor vectors includes a single recombinase recognition site while the other includes two recombinase recognition sites. Also provided are compositions for use in practicing the subject methods, including the donor and acceptor vectors themselves, as well as systems and kits that include the same. The subject invention finds use in a variety of different applications.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Methods

As summarized above, the subject invention provides recombinase-based methods for producing expression vectors. More specifically, the subject invention provides methods for producing expression vectors by combining a donor and acceptor vector that each include one or more recombinase recognition sites with a recombinase under conditions sufficient for recombinase mediated site specific recombination to occur, where such recombination results in the production of an expression vector that lacks at least a portion of the donor or acceptor vector from which it is produced, i.e., to produce a non-fusion expression vector.

A feature of the subject invention is that the donor and acceptor vectors must be able to recombine in the presence of a suitable recombinase to produce an expression vector as described above, where the expression vector lacks at least a portion of the initial donor or acceptor vector, i.e., it is a non-fusion expression vector. As such, the donor and acceptor vectors must be able to participate in a recombination event that is other than a fusion event, where by fusion event is meant an event in which two complete vectors are fused in their entirety into one fused vector, e.g., where two plasmids are fused together to produce one plasmid that includes all of material from the initial two plasmids, i.e., a fusion plasmid. As such, the subject methods are not fusion methods, where such methods are defined as those methods in which a single vector is produced from two or more initial vectors in their entirety, such that all of the initial vector material of each parent vector, e.g., plasmid, is present in its entirety in the resultant fusion vector.

The donor and acceptor vectors are further characterized in that one of the donor and acceptor vectors includes only one recombinase recognition site, while the other of the donor and acceptor vectors includes two recombinase recognition sites. In a first preferred embodiment, the donor vector includes two recombinase recognition sites while the acceptor vector includes a single recombinase recognition site. In an alternative embodiment, the donor vector includes a single recombinase recognition site while the acceptor vector includes two recombinase recognition sites. The donor and acceptor vectors of this first, preferred embodiment and this second, alternative embodiment, are described in greater detail below.

The donor and acceptor vectors described generally above may be linear or circular, e.g., plasmids, and in many embodiments of the subject invention are plasmids. Where the donor and acceptor vectors are plasmids, the donor and acceptor vectors typically range in length from about 0.2 kb to 200 kb, usually from about 2 kb to 40 kb and more usually from about 2 kb to 10 kb.

The donor and acceptor vectors are further characterized in that all of the recombinase recognition sites on the donor and acceptor vectors must be recognized by the same recombinase and should be able to recombine with each other, but within this parameter they may be the same or different, but in many embodiments are usually the same. Recombinase recognition sites, i.e., sequence-specific recombinase target sites, of interest include: Cre recombinase activity recognized sites, e.g., loxP, loxP2, loxP51 1, loxP514, loxB, loxC2, loxL, loxR, lox 86, loxΔ117; att, dif; frt; and the like. The particular recombinase recognition site is chosen, at least in part, based on the nature of the recombinase to be employed in the subject methods.

The Donor Vector

As mentioned above, in a preferred embodiment of the subject methods, the donor vector includes two recombinase recognition sites while the acceptor vector includes a single recombinase recognition site. In the donor vector of these embodiments, the donor vector includes two recombinase recognition sites, capable of recombining with each other, e.g., site 1A and site 1B, that flank or border a first or donor domain, i.e., desired donor fragment, where this domain is the portion of the vector that becomes part of the expression vector produced by the subject methods. The length of the donor domain may vary, but in many embodiments ranges from 1 kb to 200 kb, usually from about 1 kb to 10 kb. The portion of the donor vector that is not part of this donor domain, i.e., the part that is 5' of site 1A and 3' of site 1B, is referred to herein for clarity as the non-donor domain of the donor vector.

The two recombinase recognition sites of the donor vector are characterized in that they are oriented in the same direction and are capable of recombining with each other. By oriented in the same direction it is meant that they have the same head to tail orientation. Thus, the orientation of site 1A is the same as the orientation of site 1B.

The donor domain flanked by the two recombinase recognition sites, i.e., the portion of the vector 3' of the first recombinase site 1A and 5' of the second recombinase site 1B, includes at least the following components: (a) at least one restriction site and (b) at least a portion of a selectable marker, e.g. a coding sequence, a promoter, or a complete selectable marker made up of a coding sequence and a promoter. The donor domain may include at least one restriction site or a plurality of distinct restriction sites, e.g., as found in a multiple cloning site or polylinker, where by restriction site is meant a stretch of nucleotides that has a sequence that is recognized and cleaved by a restriction endonuclease. Where a plurality of restriction sites are present in the donor domain, the number of distinct or different restriction sites typically ranges from about 2 to 5, usually from about 2 to 13.

In many embodiments, there are at least two restriction sites, which may or may not be identical depending on the particular protocol employed to produce the donor plasmid, that flank a nucleic acid which is a coding sequence for a protein of interest, where the protein of interest may or may not be known, e.g., it may be a known coding sequence for a known protein or polypeptide or a coding sequence for an as yet unidentified protein or polypeptide, such as where this nucleic acid of interest is a constituent of a library, as discussed in greater detail below. The length of this nucleic acid of interest nucleic acid may vary greatly, but generally ranges from about 18 bp to 20 kb, usually from about 100 bp to 10 kb and more usually from about 1 kb to 3 kb. At least one restriction site and this nucleic acid of interest nucleic acid, when present, are sufficiently close to the 3' end of the first flanking recombinase site, i.e., recombinase recognition site 1A, such that in the expression vector produced from the donor plasmid, expression of the coding sequence of the nucleic acid of interest is driven by a promoter positioned 5' of this first recombinase site. As such, the distance separating this restriction site/nucleic acid of interest nucleic acid from the recombinase site typically ranges from about 1 bp to 150 bp, usually from about 1 bp to 50 bp.

In a first preferred embodiment, the donor domain also generally includes a portion of a selectable marker. By portion of a selectable marker is meant a sub-part of a selectable marker, e.g. a coding sequence or a promoter, which can be joined with a second subpart to produce a functioning selectable marker that confers some selectable phenotype on the host cell in which the expression vector produced by the subject methods is to be propagated. Examples of subparts of selectable markers are coding sequences and promoters. As such, in many embodiments, the portion of the selectable marker present on the donor domain is a coding sequence of a marker gene or a promoter capable of driving expression of the coding sequence of the marker gene, where in certain preferred embodiments, the coding sequence of a marker gene is the portion of the selectable marker present on the donor domain. Examples of coding sequences of interest include, but are not limited to, the coding sequences from the following marker genes:_the chloramphenicol resistance gene, the ampicillin resistance gene, the tetracycline resistance gene, the kanamycin resistance gene, the streptomycin resistance gene and the SacB gene from *B. subtilis* encoding sucrase and conferring sucrose sensitivity; and the like. The promoter portions or sub-parts of this selectable marker are any convenient promoters capable of driving expression of the selectable marker in the expression vector produced by the subject methods, see infra, and in many embodiments are bacterial promoters, where particular promoters of interest include, but are not limited to: the Ampicillin resistance promoter, the inducible lac promoter, the tet-inducible promoter from pProTet (P$_{ltetO-1}$)-available from CLONTECH, T7, T3, and SP6 promoters; and the like. The distance of this sub-part or portion of the selectable marker from the 3' end of the second recombinase recognition site, i.e., site 1B, is sufficient to provide for expression of the marker to occur in the final expression vector, where the other part of selectable marker that is required for efficient expression of the selectable marker is present on the other side, i.e., the 5' side of the adjacent recombinase recognition site. This distance typically ranges from about 1 bp to 2.5 kb, usually from about 1 bp to 500 bp.

The length of the donor domain flanked by the first and second recombinase sites of the donor plasmid, i.e., the length of the desired donor fragment, may vary greatly, so long as the above described components are present on the donor domain. Generally, the length is at least about 100 bp, usually at least about 500 bp and more usually at least about 900 bp, where the length may be as great as 100 kb or greater, but generally does not exceed about 20 kb and usually does not exceed about 10 kb. Typically, the length of the donor domain ranges from about 100 bp to 100 kb, usually from about 500 bp to 20 kb and more usually from about 900 bp to 10 kb.

In addition to the above described components, the donor vector may include a number of additional elements, where desired, that are present on the non-donor domain or non-desired donor fragment of the donor vector. For example, the non-donor domain generally includes an origin of replication. This origin of replication may be any convenient origin of replication or ori site, where a number of ori sites are known in the art, where particular sites of interest include, but are not limited to: ColE1 and its derivatives, pMB 1, other origins that function in prokaryotic cells, the yeast 2 micron origin and the like. Also present on this non-donor domain of certain preferred embodiments is a selective marker gene that provides for negative selection of the non-donor domain under particular conditions, e.g., negative selection conditions. This marker is fully functional and therefor is made up of a coding sequence operably linked to an appropriate promoter, i.e., is provided by a functional expression module or cassette. Markers of interest that are capable of providing for this negative selection include, but are not limited to: SacB, providing sensitivity to sucrose; ccdB; and the like.

This non-donor domain of the donor vector may further include one or more additional components or elements that impart additional functionality to the donor vector. For example, the donor vector may be a vector that is specifically designed for use in conjunction with a yeast two hybrid assay protocol, e.g., such that one can determine whether the gene of interest present in the donor domain encodes a product that binds to a second protein prior to transferal of the gene of interest to an expression vector. In such embodiments, the non-donor domain typically includes the following additional elements: yeast origins of replication, e.g., the yeast 2 micron origin; yeast selection markers, e.g., URA3, Leu, and trp selection markers; and peptide fragments of yeast transcription factors that are expressed as translational fusions to the gene encoded within the donor-domain; where yeast two hybrid systems are known to those of skill in the art and described in: Fields, S. and O-K. Song. 1989. A novel genetic system to detect protein-protein interactions. *Nature* 340:245–246; Fields, S. and R. Sternglanz. 1994. The two-hybrid system: an assay for protein-protein interactions. *Trends Genet.* 10: 286–292 and the MATCHMAKER system III user manual, available from CLONTECH. In other embodiments, the non-donor domain main contain yet other functional elements that provide specific functions to the donor. For example, Donor vectors can be designed that would also function as prokaryotic expression vectors that express the gene of interest encoded on the donor domain in prokaryotic cells either as a native protein or fused to an affinity or epitope tag. Such vectors may include the following elements in their non-donor domain: inducible bacterial promoters, such as the lac promoter or the P$_{ltetO-1}$ promoter; affinity or epitope tags, e.g., GST, 6x(HN), myc-tag, HA-Tag, GFP and its derivatives. Donor vectors designed to function as retroviral vectors would additionally include retroviral LTRs and packaging signals in the non-donor domain. Donor vectors for expression in mammalian cells might also encode affinity or epitope tags, e.g., GST, 6x(HN), myc-tag, HA-Tag, GFP and its derivatives; and mammalian constitive or inducible promoters, e.g., the CMV promoter, the tet-inducible promoter, the TK promoter; viral promoters, e.g., T7, T3, SP6. In a preferred embodiment of this particular embodiment of the subject invention, the donor vector is as follows. The donor-partial selectable marker comprises the open reading frame (ORF) for a selectable marker gene, and is placed between the two donor sequence-specific recombinase target sites, adjacent to the second-donor sequence-specific recombinase target site. In a more preferred embodiment of the donor construct, the open reading frame of the selectable marker is situated such that its 5' to 3' orientation is opposite that of the two donor sequence-specific recombinase target sites.

In another embodiment of the donor construct, the donor construct is a closed circle (e.g., a plasmid or cosmid) comprising, in addition to the two donor sequence-specific recombinase target sites, the unique restriction site or polylinker and the selectable marker gene open reading frame, at least one origin of replication, and at least one donor-functional selectable marker gene. The methods of the present invention should not be limited by the origin of replication selected. For example, origins such as those found in the pUC series of plasmid vectors or of the pBR322 plasmid may be used, as well as others known in the art. Those skilled in the art know that the choice of origin depends on the application for which the donor construct is intended and/or the host strain in which the construct is to be propagated.

A variety of selectable marker genes may be utilized, either for the donor-partial selectable marker or for the donor-functional selectable marker, and such genes may confer either positive- or negative-resistance phenotypes; however, the donor-partial and the donor-functional selectable marker genes should be different from one another. In a preferred embodiment, the selectable markers are selected from the group consisting of the chloramphenicol resistance gene, the ampicillin resistance gene, the tetracycline resistance gene, the kanamycin resistance gene, the streptomycin resistance gene and the sacB gene from *B. subtilis* encoding sucrase and conferring sucrose sensitivity. In a more preferred embodiment, the donor-partial selectable marker is a portion of the gene (e.g., the open reading frame) for chloramphenicol resistance and the donor-functional selectable marker gene is the gene for ampicillin resistance. In another preferred embodiment of the donor construct, the origin of replication and the donor-functional selectable marker gene lie 5' of the first-donor sequence-specific recombinase target site.

In another embodiment of the present invention, there is provided a donor construct with all the above-described features, but additionally having a marker gene different from either the donor-functional selectable marker gene or the donor-partial selectable marker gene, wherein the additional marker gene is positioned 5' of the first sequence-specific recombinase target site such that upon combination with a recombinase, the additional marker gene is located on the undesired second donor fragment. This marker gene provides an additional screen to exclude any products that result in recombinants containing the second donor fragment. The marker gene could be, for example, LacZ. In this case, incorrect recombinants would generate blue colonies on X-Gal plates. Alternatively, a more preferred additional marker would be the sacB gene conferring sucrose sensitivity. In this case, any incorrect clones would be killed when grown on sucrose containing medium. The additional marker provides another screen, thereby enhancing the system by further ensuring that only correct recombination products are obtained following recombination and transformation.

In yet another embodiment of the donor construct, the donor construct further comprises a termination sequence placed 3' of the restriction site or polylinker sequence but 5' of the second-donor sequence-specific recombinase target site. In a most preferred embodiment, the termination sequence is placed 5' of the 3' end of the donor-partial selectable marker (e.g. the ORF of the selectable marker gene in the preferred embodiment which is in the 5' to 3' orientation opposite that of both donor sequence specific recombinase target sites). The present embodiment is not be limited by the termination sequence chosen. In one embodiment, the termination sequence is the T1 termination sequence; however, a variety of termination sequences are known to the art and may be employed in the nucleic acid constructs of the present invention, including the T6S, TINT, TL1, TL2, TR1, and TR2 termination signals derived from the bacteriophage lambda, and termination signals derived from bacterial genes such as the trp gene of *E. coli*.

In another preferred embodiment of the donor construct, the donor construct further comprises a polyadenylation sequence placed 3' of the unique restriction site(s) or polylinker but 5' of the second-donor sequence-specific recombinase target site. In a most preferred embodiment, the polyadenylation sequence is placed 5' of the 3' end of the open reading frame of the selectable marker gene similar to the placement described for the termination sequence supra. The present invention should not be limited by the nature of the polyadenylation sequence chosen. In one embodiment, the polyadenylation sequence is selected from the group consisting of the bovine growth hormone polyadenylation sequence, the simian virus 40 polyadenylation sequence and the Herpes simplex virus thymidine kinase polyadenylation sequence.

Also, in a preferred embodiment, the donor construct further comprises a gene or DNA sequence of interest inserted into the unique restriction enzyme site or polylinker. The present invention should not be limited by the size of the DNA of interest inserted into the unique restriction site or polylinker nor the source of DNA (e.g., genomic libraries, cDNA libraries, etc.).

Thus, in a most preferred embodiment of the donor nucleic acid construct, there is provided, in 5' to 3' order: a) a first-donor sequence-specific recombinase target site; b) a nucleic acid or gene of interest; c) termination and polyadenylation sequences; d) an open reading frame for a selectable marker gene in a 5' to 3' orientation opposite to that of the first-donor sequence-specific recombinase target site; e) a second-donor sequence-specific recombinase target site in the same 5' to 3' orientation as the first donor sequence-specific recombinase target site, wherein the second-donor sequence-specific recombinase target site is able to recombine with said first-donor sequence-specific recombinase target site; f) an origin of replication; and g) a donor-functional selectable marker gene.

As mentioned above, in an alternative embodiment of the subject invention, the donor vector employed in the subject methods includes only a single recombinase recognition site, while the acceptor vector, described in greater detail below, includes two recombinase recognition sites. In this embodiment, the donor vector includes: a) a donor partial selectable marker element; b) one sequence-specific recombinase target site with a defined 5' to 3' orientation; and c) a unique restriction enzyme site or polylinker, said restriction enzyme site or polylinker being located 3' of the sequence-specific recombinase target site. The donor partial selectable marker element must be placed in said donor construct so that when the donor construct later recombines with the acceptor construct, a functional selectable marker is formed in the resulting final recombination product. In a preferred embodiment of this alternative embodiment, the donor partial selectable marker element comprises the open reading frame (ORF) for a selectable marker gene placed adjacent to the sequence-specific recombination site such that its 5' to 3' orientation is opposite to that of the sequence-specific recombination site. In addition, in this preferred embodiment of the alternative embodiment of the donor construct, the donor construct is a closed circle (e.g., a plasmid or cosmid) comprising, in addition to said sequence-specific recombinase target site, said unique restriction site or polylinker and said selectable marker gene open reading frame, an origin of replication capable of replicating the final recombination construct, a functional selectable marker gene driven by a promoter, a prokaryotic termination sequence placed 3' of the restriction site or polylinker sequence and a eukaryotic polyadenylation sequence placed 3' of the restriction site or polylinker. Also, in a preferred embodiment of the alternative embodiment, the donor construct further comprises a gene or DNA sequence of interest inserted into the unique restriction enzyme site or polylinker. The present invention should not be limited by the size of the DNA of interest inserted into the unique restriction site or polylinker.

Figure 2B:
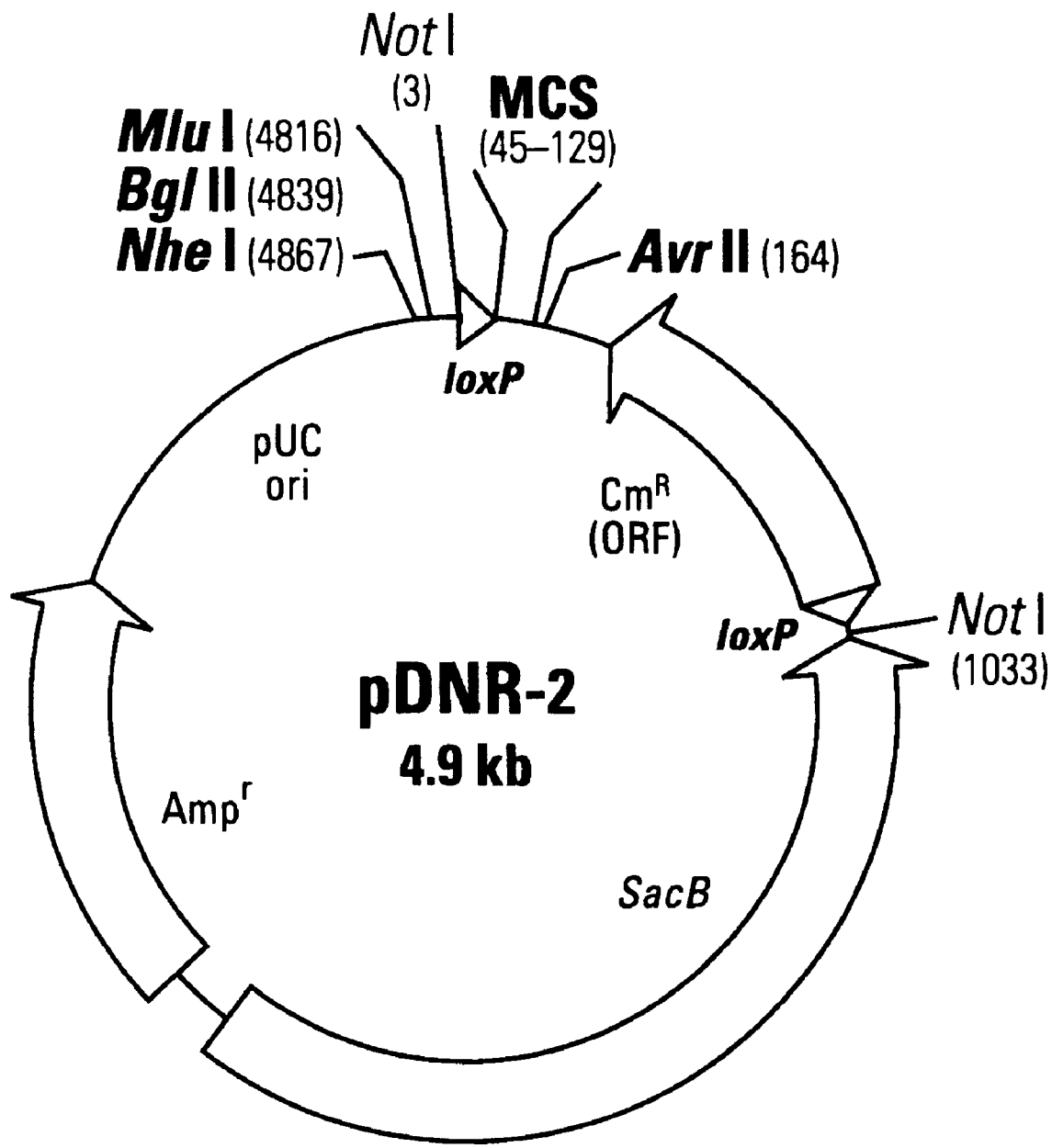
Figure 2C:
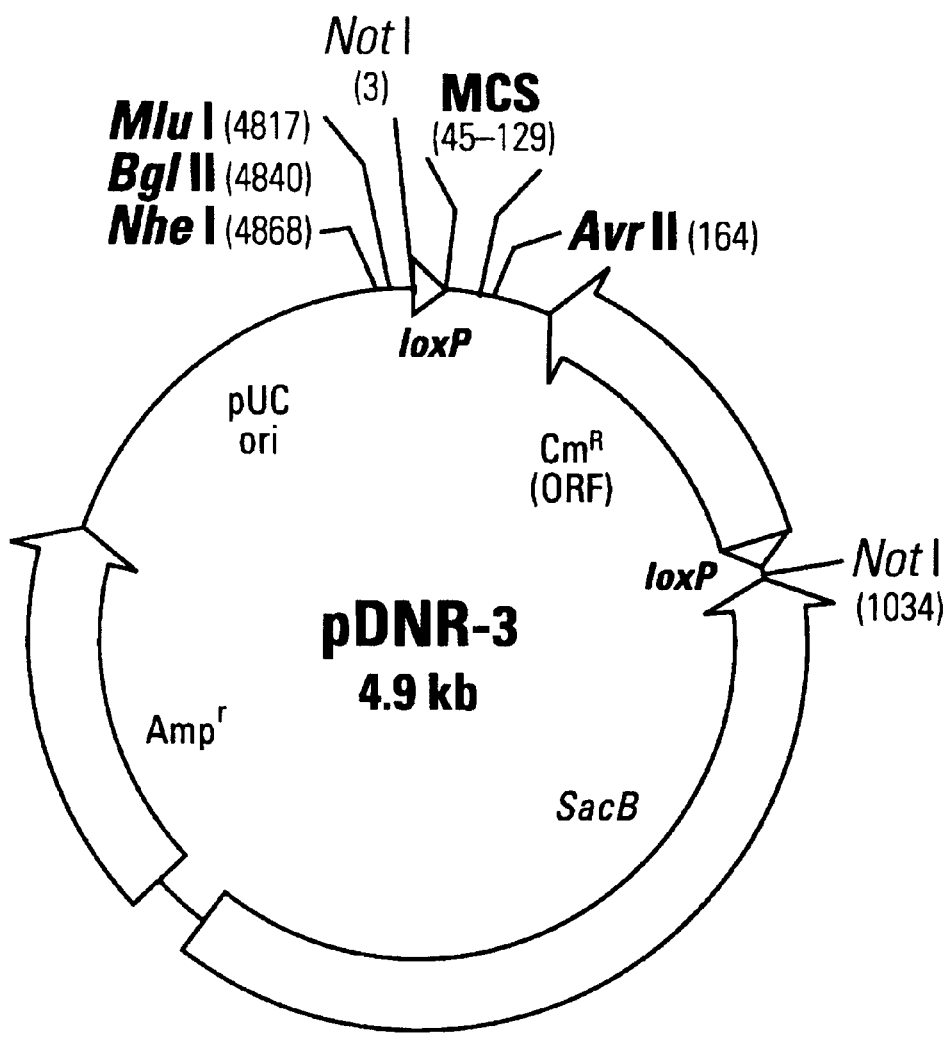

FIGS. 2A to 2C provide schematic representations of three different representative specific donor vectors, specifically donor plasmids, of the subject invention, i.e., pDNR1; pDNR2 and pDNR3. Each of these specific representative vectors includes two loxP sites oriented in the same direction. Also present in each of these specific donor plasmids is the chloramphenicol resistance open reading frame and a multiple cloning site, which elements are flanked by the lox P sites and are present on the part of the plasmid that is incorporated into the final expression vector upon practice of the subject methods. Also present on each of the donor plasmids are two selectable markers on the portion of the plasmid that is not incorporated into the final expression vector, i.e., Amp$^r$ and SacB. These three specific donor plasmids differ from each other with respect to the multiple cloning site, and specifically the open reading frame of the multiple cloning site, as shown in FIG. 1B. Yet another specific donor vector of interest is the p-DNR-Lib vector, shown in FIG. 2D. In this vector only one selectable marker is present on the portion of the plasmid that is not incorporated into the final expression vector, e.g., SacB.

The Acceptor Vector

As mentioned above, in a preferred embodiment of the subject invention, the acceptor vector employed in the subject methods is a vector that includes a single recombinase site. In these embodiments, the single recombinase site is flanked on one side by a promoter and on the other side, in certain preferred embodiments, by a portion of a selectable marker, e.g., a promoter or a coding sequence, where in many preferred embodiments described further below, this portion or sub-part of the selectable marker is a second promoter, e.g., a bacterial promoter. In these embodiments, the single recombinase site is flanked by two oppositely oriented promoters, where one of promoters drives expression of the gene of interest in the expression vector produced by the subject methods and the second promoter drives expression of the coding sequence of the recombinant-functional selectable marker in the expression vector produced by the subject methods. In these embodiments, the first promoter is a promoter that is capable of driving expression of the gene of interest in the expression vector, where representative promoters include, but are not limited to the CMV promoter, the tet-inducible promoter; retroviral LTR promoter/enhancer sequences, the TK promoter, bacterial promoters, e.g. the lac promoter, the $P_{LtetO\text{-}1}$ promoter; the yeast ADH promoter and the like. The distance between the first promoter and the recombinase site is one that allows for expression in the final expression vector, where the distance typically ranges from about 1 bp to 1000 bp, usually from about 10 bp to 500 bp. The second promoter is a promoter that is capable of driving expression of the recombinant-functional selectable marker, and is generally a bacterial promoter. Bacterial promoters of interest include, but are not limited to: the Ampicillin promoter, the lac promoter, the $P_{LtetO\text{-}1}$ promoter, the T7 promoter and the like. The distance between the bacterial promoter and the recombinase site is sufficient to provide for expression of the selectable marker in the expression vector and typically ranges from about 1 bp to 2.5 kb, usually from about 1 bp to 200 bp.

As indicated above, in yet other preferred embodiments the acceptor vector lacks the portion or subpart of the selectable marker. In these embodiments, the acceptor vector may be used with a donor vector that includes a complete positive selectable marker in the desired donor fragment flanked by the two recombinase sites, i.e., the donor vector portion located between the 3' end of the first recombinase site and the 5' end of the second recombinase site. Alternatively, the acceptor vector may be used with a donor vector that only includes a partial selectable positive marker, as described above, where the partial marker is nonetheless functional in the resultant expression vector.

The acceptor vector of the embodiments described above may include a number of additional components or elements which are requisite or desired depending on the nature of the expression vector to be produced from the acceptor vector. In many embodiments of the subject invention, the acceptor vector is an acceptor nucleic acid construct comprising: a) an origin of replication capable of replicating the final desired recombination construct or expression vector; b) an acceptor sequence-specific recombinase target site having a defined 5' to 3' orientation; c) a first promoter adjacent to the 5' end of the acceptor sequence-specific recombinase target site; and d) an acceptor-partial selectable marker, wherein the acceptor-partial selectable marker is capable of recombining with a donor-partial selectable marker from a donor construct (or first donor fragment, once the donor construct is resolved) so creating a recombinant-functional selectable marker in a final desired recombination construct. As in the donor construct, the acceptor construct is not limited by the nature of the sequence-specific recombinase target site employed, and in preferred embodiments the sequence-specific recombinase target site may be selected from the group consisting of loxP, loxP2, loxP511, loxP514, loxB, loxC2, loxL, loxR, loxΔ86, loxΔ117, loxP3, loxP23, att, dif, and frt. The acceptor sequence-specific recombinase target site from the acceptor construct does not have to be identical to those on the donor construct; however, the sequence-specific recombinase target sites on the acceptor and donor constructs must be able to recombine with each other.

In a preferred embodiment, the acceptor-partial selectable marker is a second promoter, wherein the second promoter is oriented such that its 5' to 3' orientation is opposite that of the acceptor sequence-specific recombinase target site and the first promoter, and wherein the 3' end of the second promoter is adjacent to the 3' end of the acceptor sequence-specific recombinase target site.

The acceptor construct is not limited by the nature of the origin of replication employed. A variety of origins of replication are known in the art and may be employed on the acceptor nucleic acid constructs of the present invention.

Those skilled in the art know that the choice of origin depends on the application for which the acceptor construct is intended and/or the host strain in which the construct is to be propagated. In the case of the acceptor construct, the origin of replication is chosen appropriately such that both the acceptor construct and the final desired recombination construct will be able to replicate in the given host cell.

The acceptor construct also is not limited by the nature of the promoters employed. Those skilled in the art know that the choice of the promoter depends upon the type of host cell to be employed for expressing a gene(s) under the transcriptional control of the chosen promoter. A wide variety of promoters functional in viruses, prokaryotic cells and eukaryotic cells are known in the art and may be employed in the acceptor nucleic acid constructs of the present invention. In a preferred embodiment of the invention, the donor construct contains a gene or DNA sequences of interest and when the donor construct recombines with the acceptor construct, the first promoter of the acceptor construct is positioned such that it will drive expression of the gene or DNA sequences of interest. Thus, a promoter capable of driving the gene or DNA sequences of interest should be chosen for the first promoter. Further, in a preferred embodiment of the present invention, the acceptor-partial selectable marker is a promoter capable of driving the expression of the donor-partial selectable marker ORF from the donor construct (e.g., the promoter for the ampicillin gene from the plasmid pUC19) or a viral promoter including, but not limited to, the T7, T3, and Sp6 promoters.

In yet another preferred embodiment of the acceptor construct, the acceptor construct additionally includes a DNA sequence encoding a peptide affinity domain or peptide tag sequence, wherein the affinity domain or tag sequence is 3' of the first promoter and 5' of the acceptor sequence-specific recombinase target site, such that the expression of the affinity domain or tag sequence is under control of the first promoter, and such that it is in the same translational frame as the acceptor sequence-specific recombinase target site. The present invention is not limited by the nature of the affinity domain or tag sequence employed; a variety of suitable affinity domains are known in the art, including glutathione-S-transferase, the maltose binding protein, protein A, protein L, polyhistidine tracts, etc.; and tag sequences include, but are not limited to the c-Myc Tag, the HA Tag, the FLAG tag, Green Fluorescent Protein (GFP), etc.

In another preferred embodiment of the acceptor construct, the acceptor construct further includes an acceptor-functional selectable marker. The present invention is not limited by the nature of the acceptor-functional selectable marker chosen and the selectable marker gene may result in positive or negative selection. In a preferred embodiment, the acceptor-functional selectable marker gene is selected from the group consisting of the chloramphenicol resistance gene, the ampicillin resistance gene, the tetracycline resistance gene, the kanamycin resistance gene, the streptomycin resistance gene and the sacB gene.

Figure 3A:
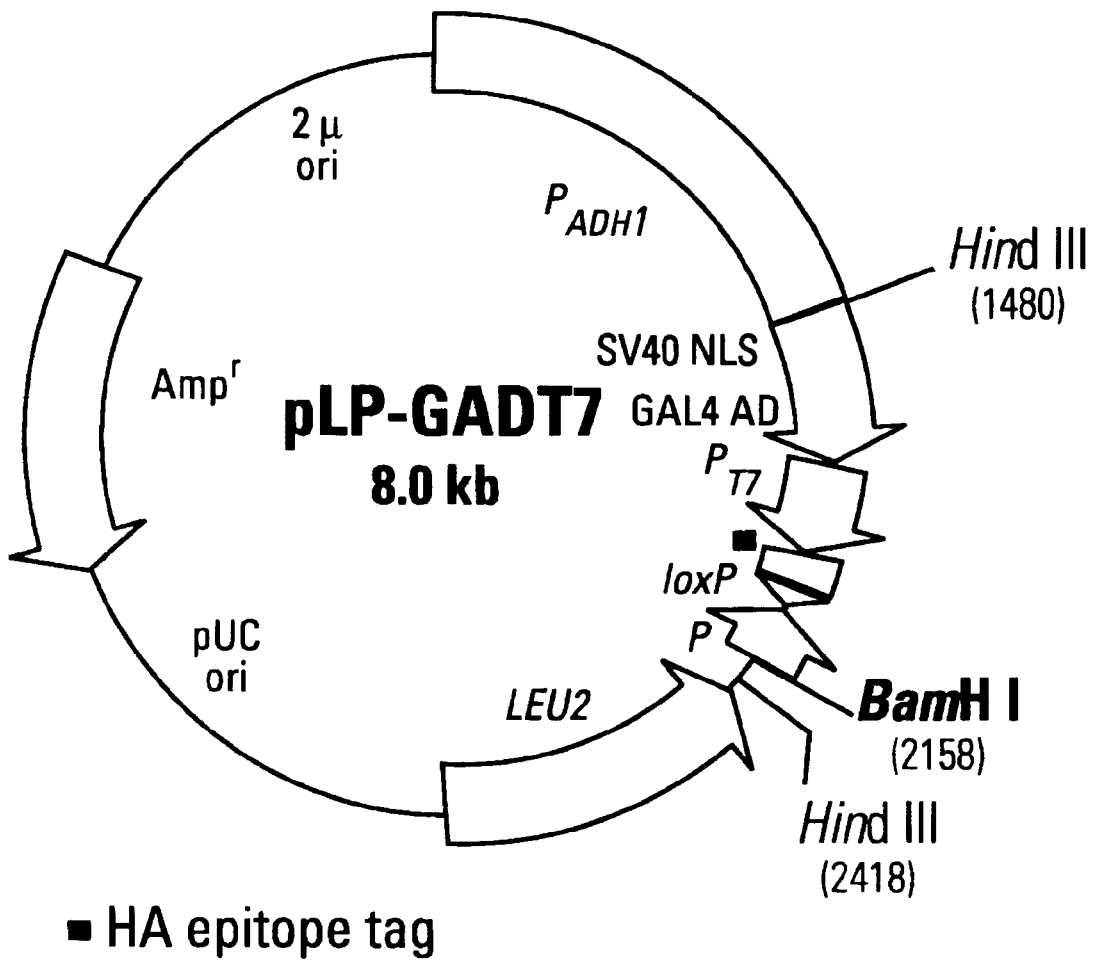
Figure 3B:
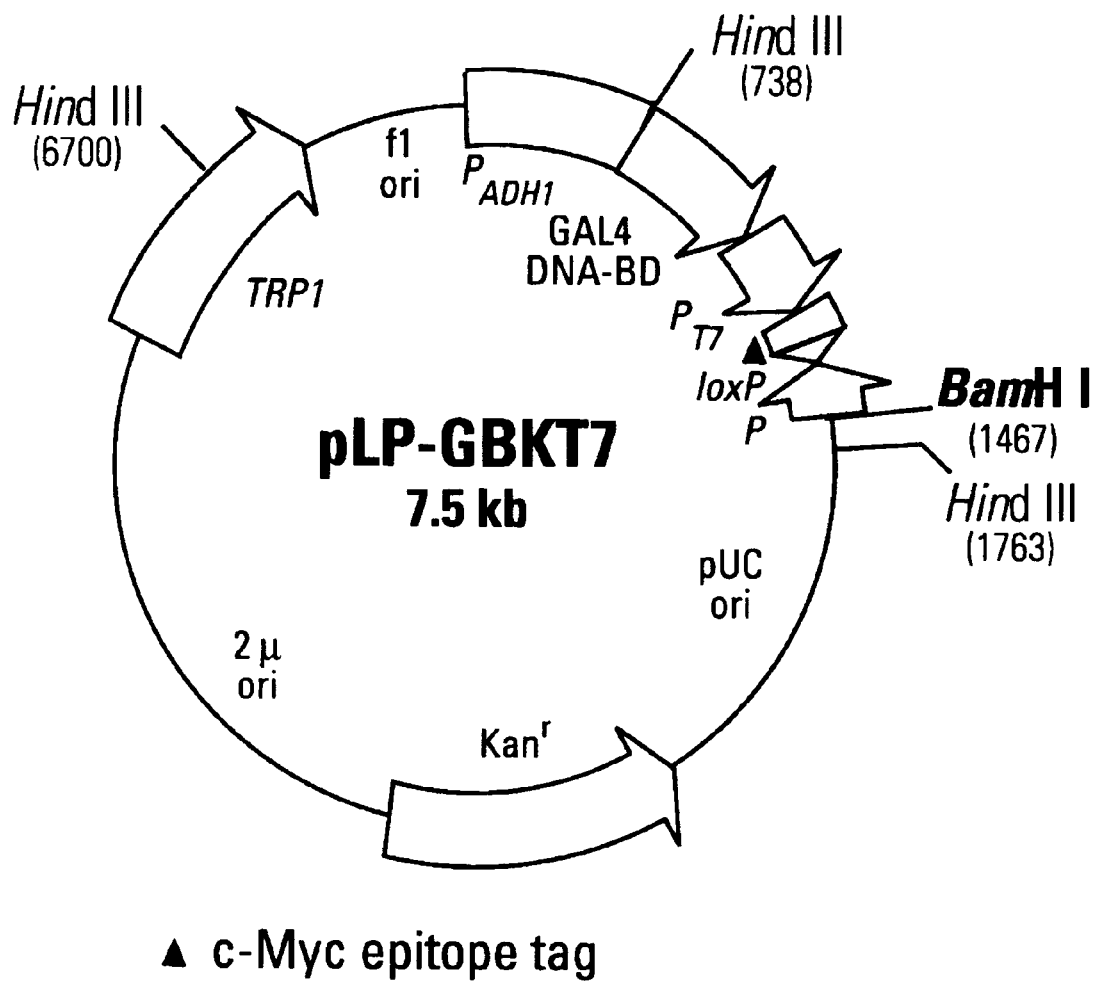
Figure 3C:
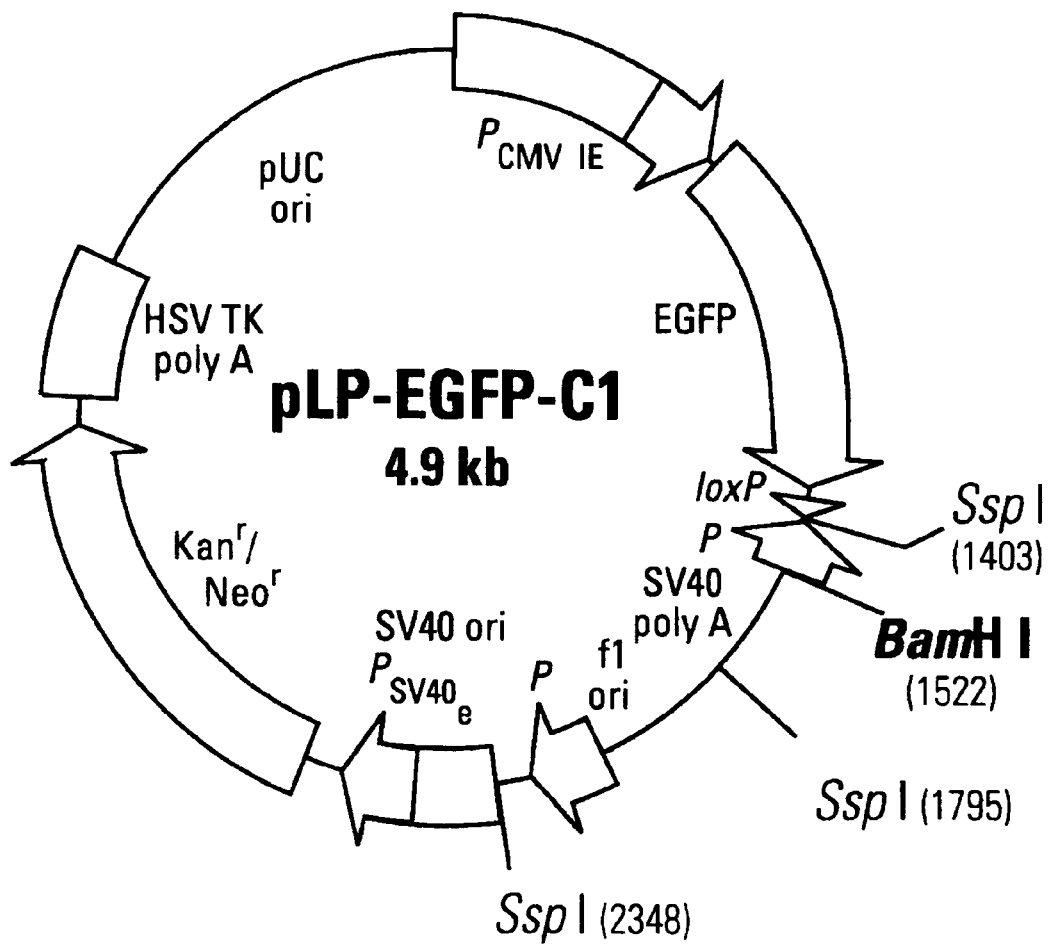
Figure 3D:
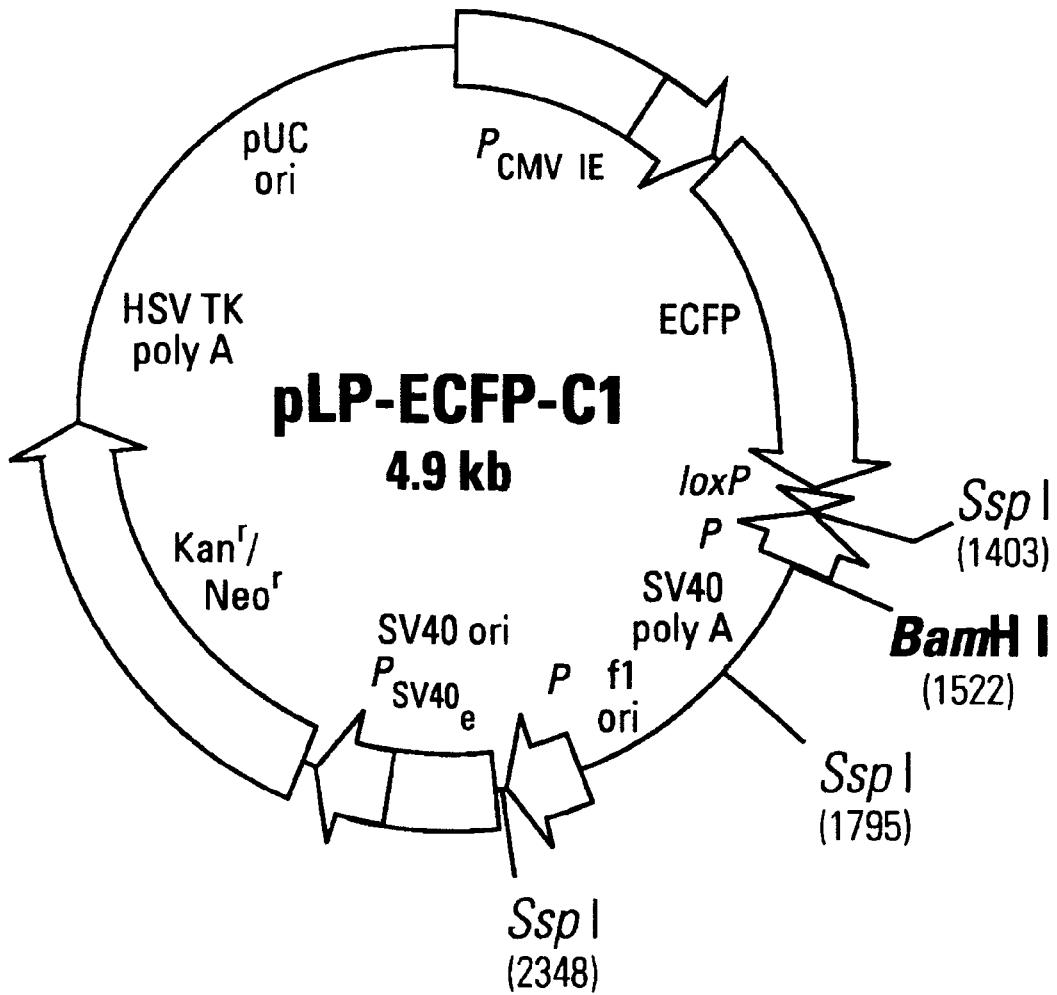
Figure 3E:
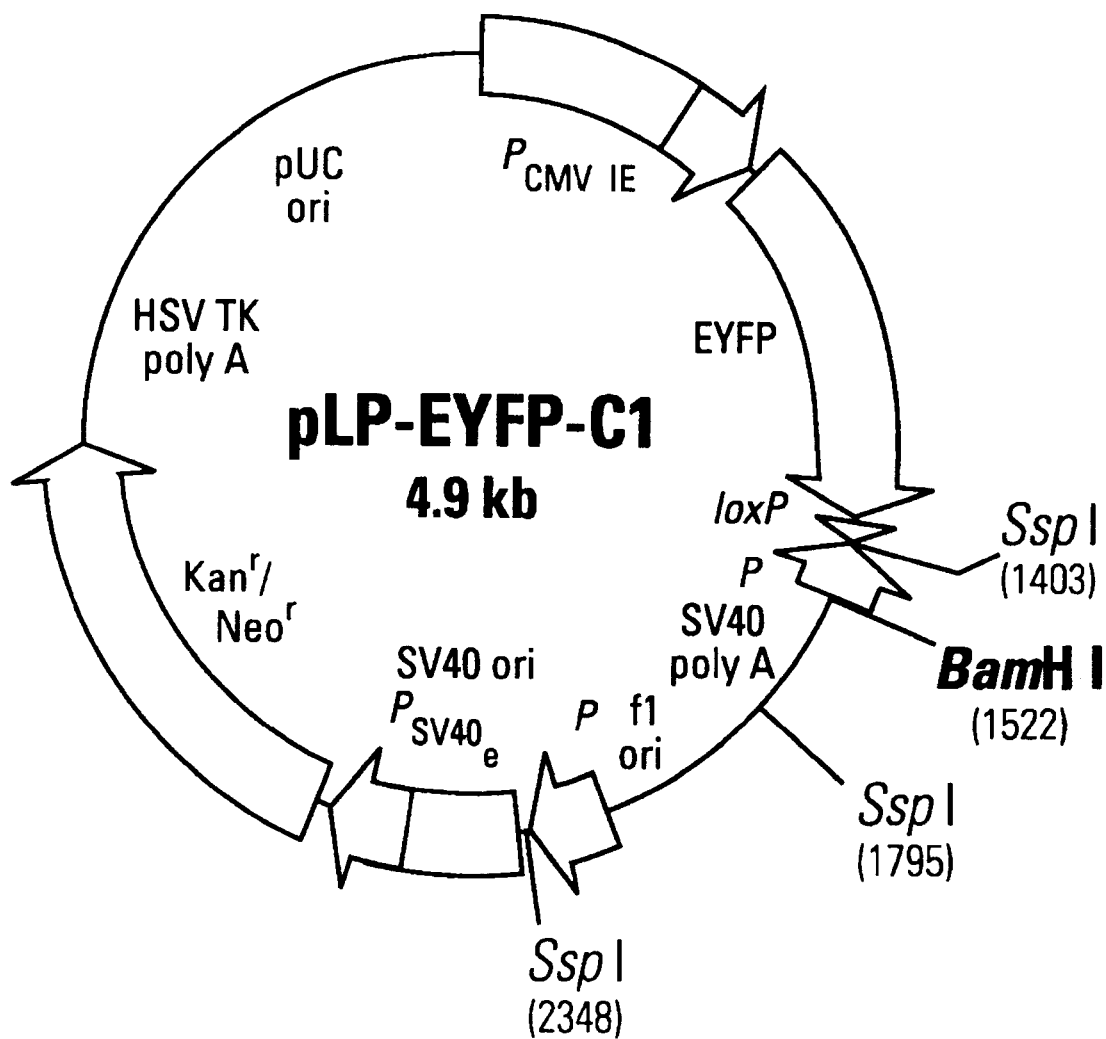
Figure 3F:
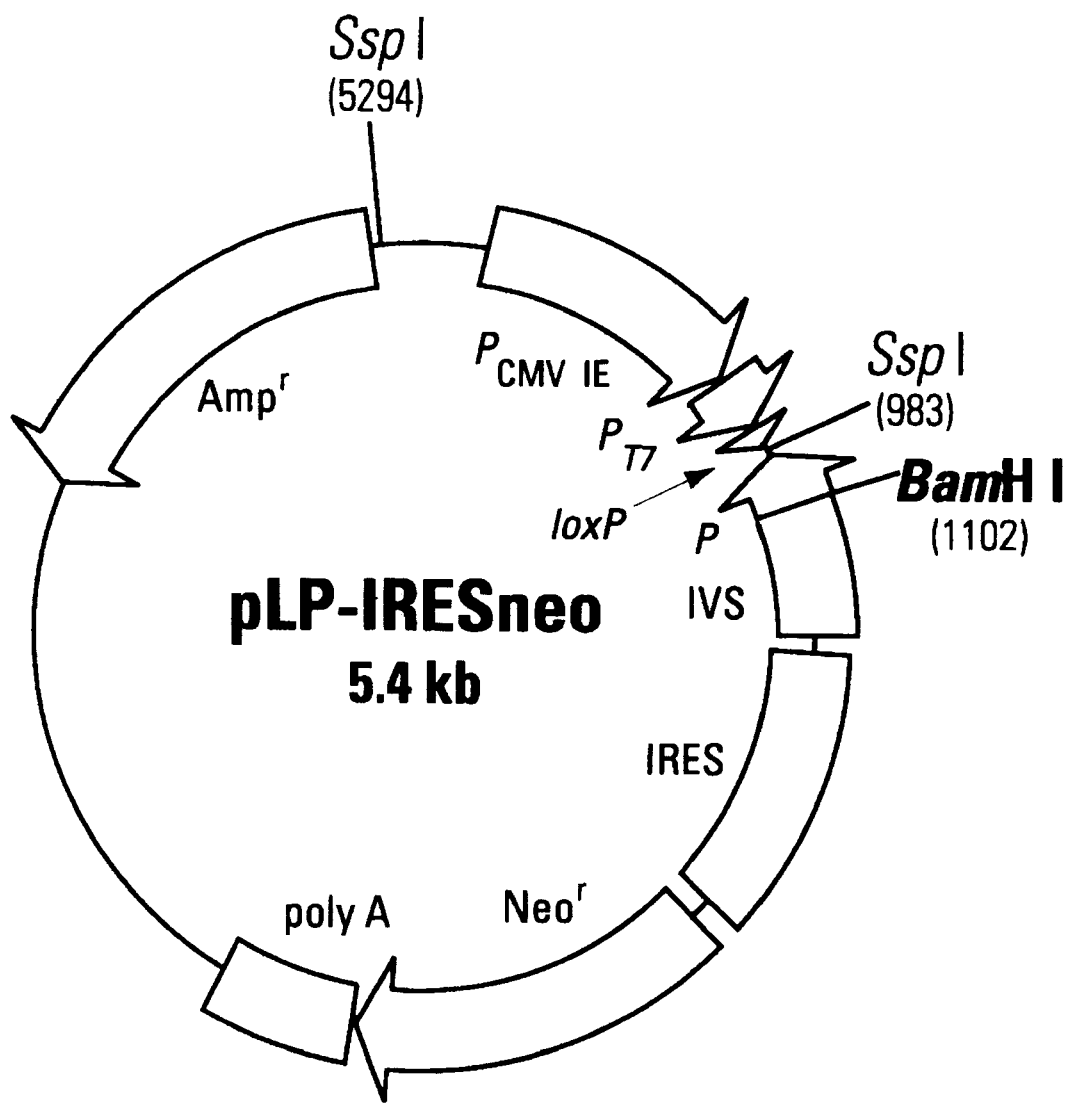
Figure 3G:
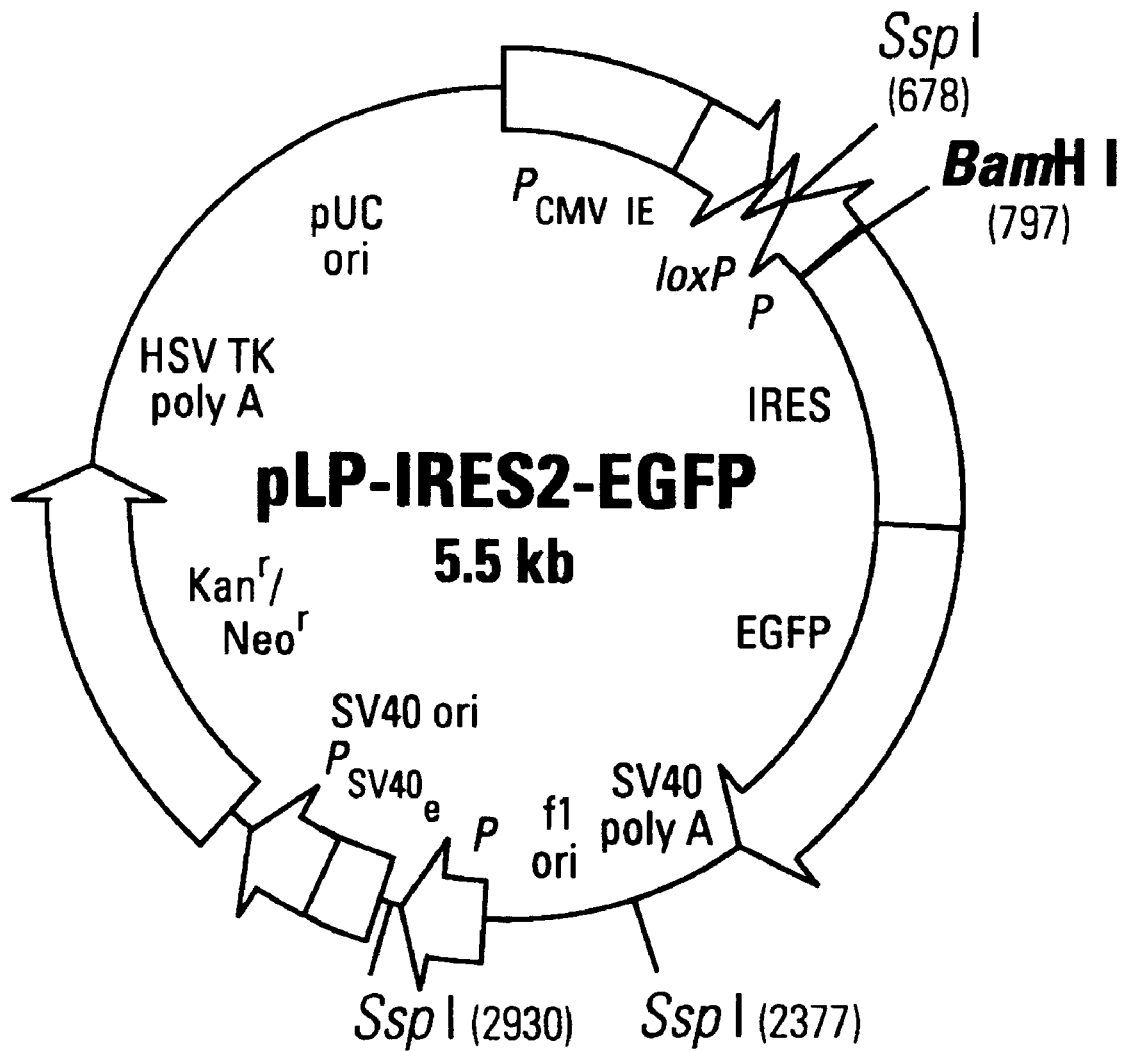
Figure 3H:
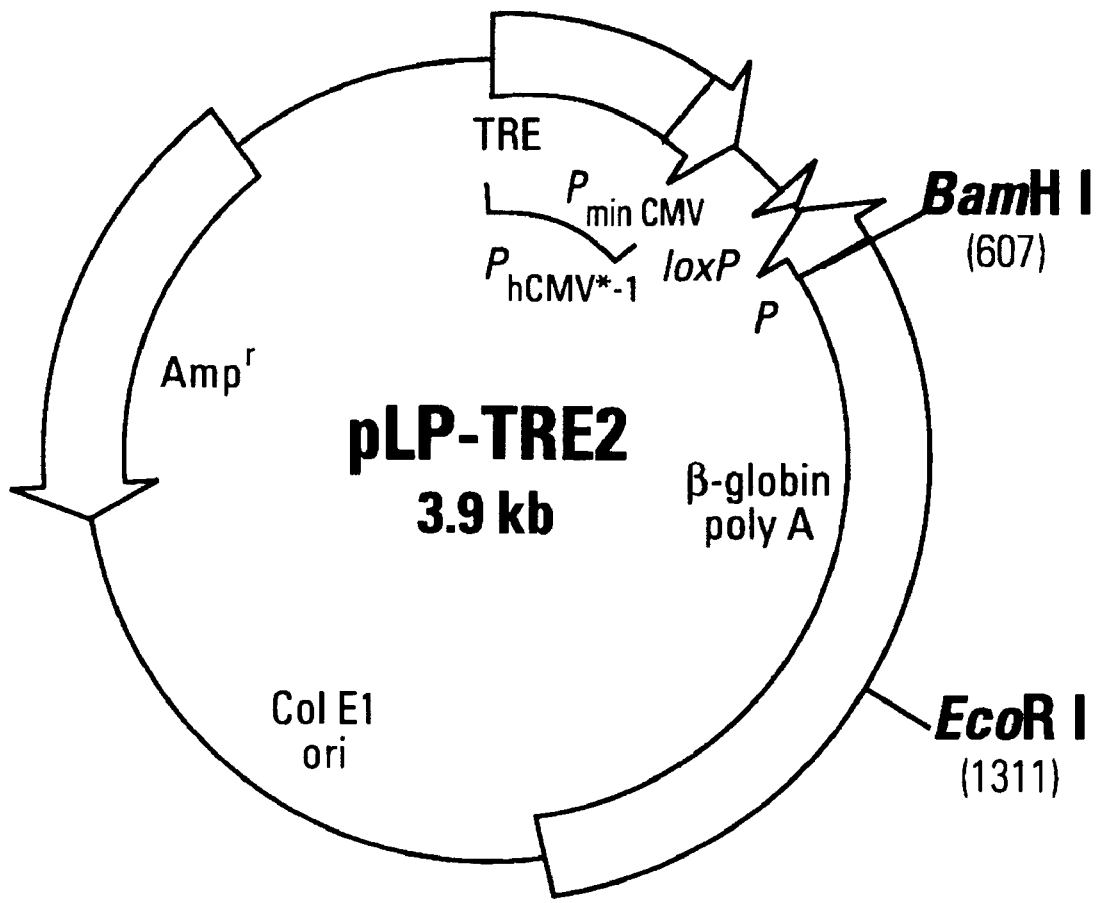
Figure 31:
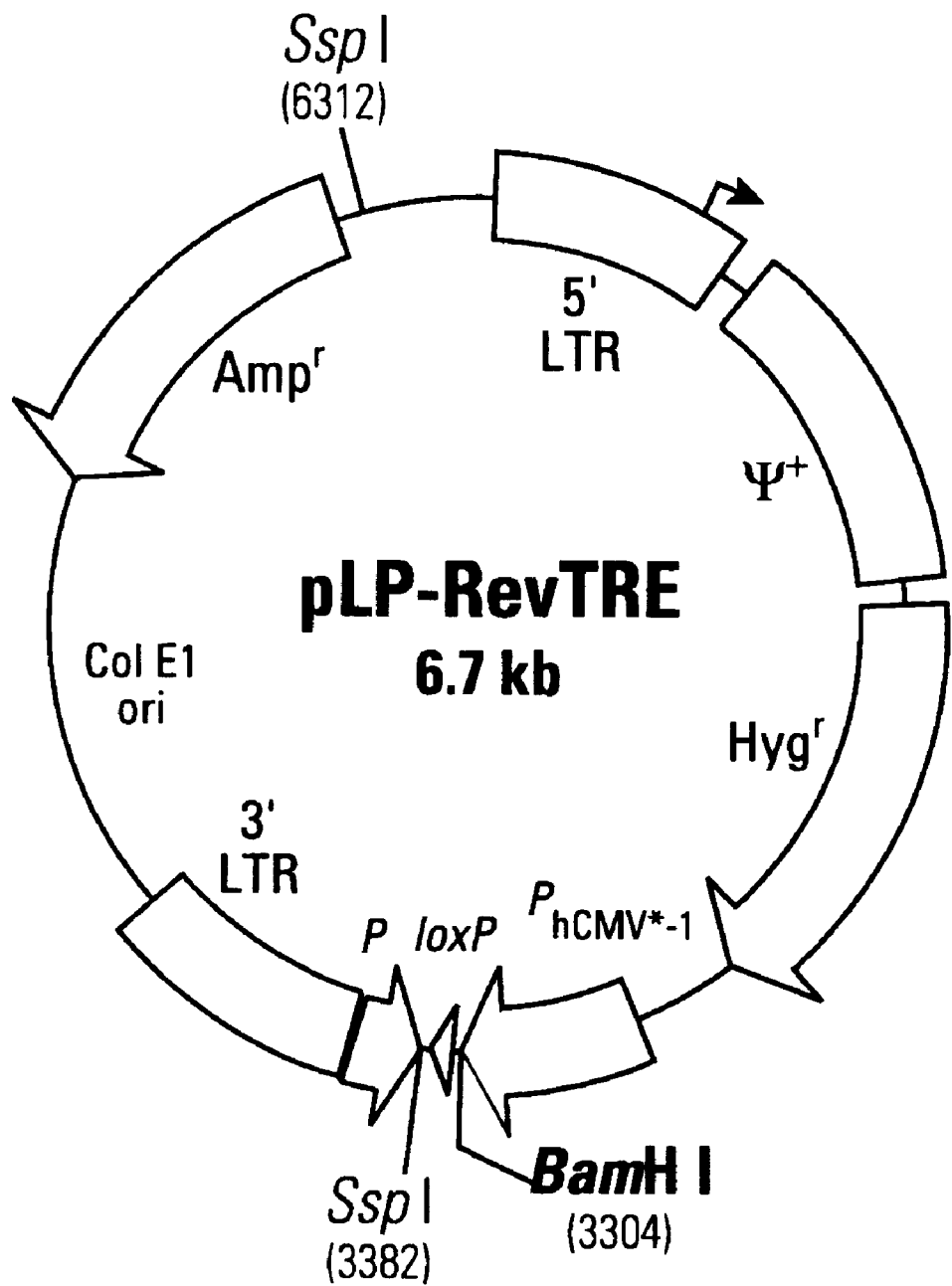
Figure 3J:
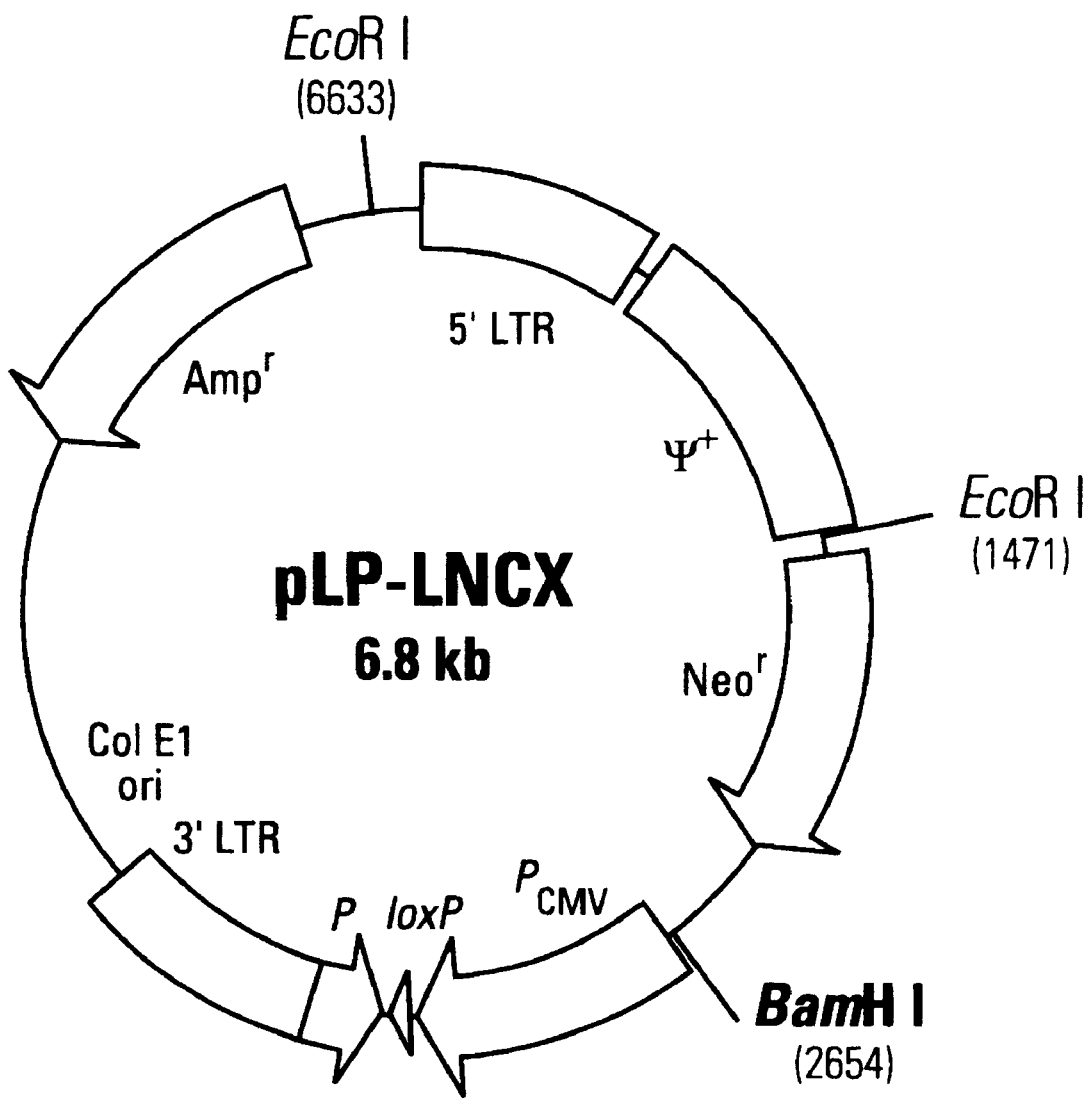

In addition to one or more of the above described components, the acceptor vectors may include a number of additional components that impart specific function to the expression vectors that are produced from the acceptor vector according to the subject methods. Additional elements that may be present on the subject acceptor vectors include, but are not limited to: (a) elements requisite for generating vectors suitable for use in yeast two hybrid expression assays, e.g., a GAL4 activation domain coding sequence, a GAL4 DNA-binding domain coding sequence, (as found in pLP-GADT7 and pLP-GBKT7 shown in FIGS. 3A & 3B); (b) elements necessary for study of the localization of a protein in a cell, e.g., tagging elements such as fluorescent protein coding sequences, such as the GFP coding sequences (as found in pLP-EGFP-C1, pLP-ECFP-C1 and pLP-EYFP-C1 shown in FIGS. 3C to 3E); (c) elements necessary for constitutive, bicistronic expression in mammalian cells, e.g., IRES sites, in combination with selectable markers, e.g. antibiotic resistance, fluorescent protein, etc. (as found in pLP-IRESneo and pLP-IRES2-EGFP shown in FIGS. 3F to 3G); (d) elements necessary for inducible expression of the gene of interest on an expression vector, e.g. inducible promoters such as the tet-responsive promoter, etc. (as illustrated by pLP-TRE2, pLP-ProTet and pLP-RevTRE, shown in FIGS. 3H, 3I and 3K); (e) elements that provide for retroviral expression vectors, e.g., as found in pLP-LNCX and pLP-RevTre shown in FIGS. 3I and 3J; and the like.

Also provided is an alternative acceptor construct embodiment that can be used with the alternative donor vector described above. In this embodiment, the alternative acceptor construct includes: a) an origin of replication; b) a first sequence-specific recombinase target site and a second sequence-specific recombinase target site each having a 5' and a 3' orientation, wherein said first and second sequence-specific recombinase target sites have the same 5' to 3' orientation and where said first and second sequence-specific recombinase target sites can recombine with each other and with the sequence-specific recombinase target site of said alternative donor construct; c) a first promoter element having the same 5' to 3' orientation as the sequence-specific recombinase target sites and wherein said first promoter element is positioned at the 5' end of said second sequence-specific recombination target site; and d) an acceptor partial selectable marker element wherein said acceptor partial selectable marker element is capable of recombining with said donor partial selectable marker element from said alternative donor construct to create a functional selectable marker element in the final recombination construct. In a preferred embodiment of this alternative embodiment, said acceptor partial selectable marker element is a second promoter having a 5' and 3' end, wherein said second promoter is oriented such that its 5' to 3' orientation is opposite to that of said acceptor sequence-specific recombination sites and said first promoter element, and wherein the 3' end of said second promoter is adjacent to the 3' end of the first sequence-specific recombination site. Also in a preferred embodiment of the alternative embodiment of the acceptor construct, the acceptor construct additionally comprises a DNA sequence encoding a peptide affinity domain or peptide tag sequence, wherein said affinity domain is under control of the said first promoter element and is in the same translational frame as the second sequence-specific recombinase site. Also, a preferred embodiment of the alternative embodiment of the acceptor construct further comprises a functional selectable marker gene.

Expression Vector Generation with a Recombinase

As mentioned above, in the subject methods the donor and acceptor vectors are contacted with a recombinase under conditions sufficient for site specific recombination to occur, specifically under conditions sufficient for a recombinase mediated recombination event to occur that produces the desired expression vector, where expression vector production is accomplished without cutting or ligation of the donor and acceptor vectors with restriction endonucleases and nucleic acid ligases. The contact may occur under in vitro or in vivo conditions, as is desired and/or convenient.

In many embodiments, an aqueous reaction mixture is produced by combining the donor and acceptor vectors and the recombinase with water and other requisite and/or desired components to produce a reaction mixture that, under appropriate conditions, results in production of the desired expression vector. The various components may be combined separately or simultaneously, depending on the nature of the particular component and how the components are combined. Conveniently, the components of the reaction mixture are combined in a suitable container. The amount of donor and acceptor vectors that are present in the reaction mixture are sufficient to provide for the desired production of the expression vector product, where the amounts of donor and acceptor vector may be the same or different, but are in many embodiments substantially the same if not the same. In many embodiments, the amount of donor and acceptor vector that is present in the reaction mixture ranges from about 50 ng to 2 ug, usually from about 100 ng to 500 ng and more usually from about 150 ng to 300 ng, for a reaction volume ranging from about 5 $\mu$l to 1000 $\mu$l, usually from about 10 $\mu$l to 50 $\mu$l.

The recombinase that is present in the reaction mixture is one that provides for recombination of the donor and acceptor vectors, i.e. one that recognizes the recombinase recognition sites on the donor and acceptor vectors. As such, the recombinase employed will vary, where representative recombinases include, but are not limited to: recombinases, transposes and integrases, where specific recombinases of interest include, but are not limited to: Cre recombinase (the cre gene has been cloned and expressed in a variety of hosts, and the enzyme can be purified to homogeneity using standard techniques known in the art—purified Cre protein is available commercially from Novagen); FLP recombinase of S. cerevisiae that recognizes the frt site; Int recombinase of bacteriophage Lambda that recognizes the att site; xerC and xerD recombinases of E. coli, which together form a recombinase that recognizes the dif site. the Int protein from the Tn916 transposon; the Tn3 resolvase, the Hin recombinase; the Cin recombinase; the immunoglobulin recombinases; and the like. While the amount of recombinase present in the reaction mixture may vary depending on the particular recombinase employed, in many embodiments the amount ranges from about 0.1 units to 1250 units, usually from about 1 unit to 10 units and more usually from about 1 unit to 2 units, for the above described reaction volumes. The aqueous reaction mixture may include additional components, e.g., a reaction buffer or components thereof, e.g., buffering compounds, such as Tris-HCl; MES; sodium phosphate buffer, sodium acetate buffer; and the like, which are often present in amounts ranging from about 10_mM to 100 mM, usually from about 20 mM to _50 mM; monovalent ions, e.g., sodium, chloride, and the like, which are typically present in amounts ranging from about 10 mM to 500 mM, usually from about 30 mM to 150 mM; divalent cations, e.g., magnesium, calcium and the like, which are often present in amounts ranging from about 1 mM to 20 mM, usually from about 5 mM to 10 mM; and other components, e.g., BSA, EDTA, spermidine and the like; etc (where the above amount ranges are provided for the representative reaction volumes described above). As the reaction mixtures are aqueous reaction mixtures, they also include water.

The subject reaction mixtures are typically prepared at temperatures ranging from about 0–4° C., e.g., on ice, to minimize enzyme activity. Following reaction mixture preparation, the temperature of the reaction mixture is typically raised to a temperature that provides for optimum or maximal recombinase activity, and concomitantly expression vector production. Often, in this portion of the method the temperature will be raised to a temperature ranging from about 4° C. to 37° C., usually from about 10° C. to 25° C., where the mixture will be maintained at this temperature for a period of time sufficient for the desired amount of expression vector production to occur, e.g., for a period of time ranging from about 5 mins to 60 mins, usually from about 10 mins to 15 mins. Following the incubation period, the reaction mixture is subjected to conditions sufficient to inactivate the recombinase, e.g., the temperature of the reaction mixture may be raised to a value ranging from about 65° C. to 70° C. for a period of time ranging from about 5 mins to 10 mins.

Alternatively, contact of the donor and acceptor vectors with the recombinase may occur in vivo, where the donor and acceptor vectors are introduced in a suitable host cell that expresses a recombinase. In this embodiment, the recombination between the donor and acceptor vectors may be accomplished in vivo using a host cell that transiently or constitutively expresses the appropriate site-specific recombinase (e.g., Cre recombinase expressed in the bacterial strain BNN132, available from CLONTECH). pDonor and pAcceptor, i.e., the donor and acceptor vectors respectively, are co-transformed into the host cell using a variety of methods known in the art (e.g., transformation of cells made competent by treatment with $CaCl_2$, electroporation, etc.). The co-transformed host cells are grown under conditions which select for the presence of the recombinant-functional selectable marker created by recombination of pDonor with the pAcceptor (e.g., growth in the presence of chloramphenicol when the pDonor vector contains all or part of the chloramphenicol resistance gene open reading frame and pAcceptor may also contain a promoter necessary for expression of the chloramphenicol open frame). Plasmid DNA is isolated from host cells which grow in the presence of the selective pressure and is subjected to restriction enzyme digestion to confirm that the desired recombination event has occurred.

The present invention also provides a method for the in vitro recombination of nucleic acid constructs, comprising the steps of: a) providing i) a donor nucleic acid construct comprising a donor-partial selectable marker, two donor sequence-specific recombinase target sites each having a defined 5' to 3' orientation and wherein the donor sequence-specific recombinase target sites are placed in the donor construct such that they have the same 5' to 3' orientation, and a unique restriction enzyme site or polylinker, the restriction enzyme site or polylinker being located 3' of the first-donor sequence-specific recombinase target site and 5' of the second-donor sequence-specific recombinase target site; (ii) an acceptor nucleic acid construct comprising an origin of replication, an acceptor sequence-specific recombinase target site having a defined 5' to 3' orientation, a first promoter adjacent to the 5' end of the acceptor sequence-specific recombinase target site, and an acceptor-partial selectable marker, wherein the acceptor-partial selectable marker is capable of recombining with the donor-partial selectable marker from the donor construct to create a recombinant-functional selectable marker in a final desired recombination construct; b) contacting the donor and acceptor constructs in vitro with a site-specific recombinase under conditions such that the desired donor fragment recombines with the acceptor construct to form a final desired recombination construct.

The present invention further provides a method for the recombination of nucleic acid constructs in a host, comprising the steps of: a) providing i) a donor nucleic acid construct comprising a donor-partial selectable marker, two donor sequence-specific recombinase target sites each having a defined 5' to 3' orientation and wherein the donor sequence-specific recombinase target sites are placed in the donor construct such that they have the same 5' to 3' orientation, and a unique restriction enzyme site or polylinker, the restriction enzyme site or polylinker located 3' of the first-donor sequence-specific recombinase target site and 5' of the second-donor sequence-specific recombinase target site; (ii) an acceptor nucleic acid construct comprising an origin of replication, an acceptor sequence-specific recombinase target site having a defined 5' to 3' orientation, a first promoter adjacent to the 5' end of the acceptor sequence-specific recombinase target site, and an acceptor-partial selectable marker, wherein the acceptor-partial selectable marker is capable of recombining with the donor-partial selectable marker from the donor to create a recombinant-functional selectable marker in a final desired recombination construct; and iii) a host cell expressing a site-specific recombinase; b) introducing the donor and acceptor constructs into the host cell under conditions such that the desired donor fragment recombines with the acceptor construct to form the final desired recombination construct which is capable of imparting the ability to the host cell to grow in selective growth medium.

The above methods of producing expression vectors can be employed to rapidly produce a plurality of different expression vectors that are distinct from each other but carry the same coding sequence of interest from a single, original type of donor vector. In other words, the subject methods can be used to rapidly clone a nucleic acid of interest from an initial vector into a plurality of expression vectors. By plurality is meant at least 2, usually at least 5, and more usually at least 10, where the number may be as high as 20, 96 or more. The methods can be performed by one person in a period of time that is a fraction of what it would take by that person of skill in the art to produce the same number and variety of expression vectors using traditional cutting and ligation protocols, where the increase in efficiency obtained by the subject methods is at least about 6 fold, usually at least about 15 fold and more usually at least about 30 fold.

The Resultant Expression Vector

The above steps result in the production of an expression vector from donor and acceptor vectors, and more specifically from a portion of one of these vectors and the entirety of the other of these vectors, e.g., from a portion of the donor vector and the entirety of the acceptor vector, where by portion is meant the part of the donor vector that lies 3' of the first donor sequence-specific recombinase site and 5' of the second donor sequence-specific recombinase site. The size of the expression vector may vary, depending on the nature of the vector. Where the vector is a plasmid, the size of the expression vector may range from about 3 kb to 20 kb, usually from about 4 kb to 8 kb.

The resultant expression vector is characterized in that it includes two recombinase recognition sites, i.e., a first and second recombinase recognition site, oriented in the same direction. The distance between the first and second recombinase sites, specifically the distance between the 3' end of the first recombinase site and the 5' end of the second recombinase site, ranges in many embodiments from about 100 bp to 100 kb, usually from about 500 bp to 20 kb, depending on whether the coding sequence of a protein of interest or just a restriction site/multiple cloning site, is present between the first and second recombinase recognition sites. The portion of the vector that lies in this inter recombinase region, i.e. 3' of the first recombinase site and 5' of the second recombinase site, typically makes up from about 2% to 85%, usually from about 20% to 60% of the entire expression vector.

In many embodiments, the expression vector is further characterized in that 5' of the first recombinase site is a first promoter, 3' of the first recombinase site is at least one restriction site; and the second recombinase site located inside a functional selectable marker, i.e., it is flanked by disparate portions or sub-parts of a selectable marker expression module or cassette (e.g., a promoter and a coding sequence), where the second recombinase site is present between the two sub-parts of the selectable marker in a manner such that the selectable marker is functional, i.e., the coding sequence of the selectable marker is expressed. In other words the expression vector includes a selectable marker expression cassette or module made up of a promoter and coding sequence that flank the second recombinase site. In many embodiments, the second recombinase site is flanked by a promoter on its 3' end and a coding sequence of the selectable marker on its 5' end. In this embodiment, the first and second promoters, located 5' of the first recombinase site and 3' of the second recombinase site, respectively, are oriented in opposite directions.

The expression vector is further characterized by having at least one restriction site, and generally a multiple cloning site, located between the first and second recombinase sites. In many embodiments, located between the first and second recombinase sites, and flanked by two restriction sites, which may or may not be the same, is a nucleic acid of interest, i.e., gene of interest, that includes a coding sequence for a protein of interest whose expression from the expression vector is desired. In these embodiments, the first promoter 5' of the first recombinase site and the coding sequence for the protein of interest are arranged on either side of the first recombinase site such that they form an expression module or cassette that expresses the encoded protein, i.e., the coding sequence and first promoter flank the first recombinase site in manner such that they are operably linked.

In addition to the above features, the expression vector further includes at least one origin of replication that provides for replication in the host or hosts into which it is placed or transformed during use. Origins of replication of interest include, but are not limited to, those described above in connection with the donor and acceptor vectors.

In a specific embodiment, the expression vector or final construct is characterized as follows—this final desired recombination construct comprises, in operable 5' to 3' order: a) a first promoter; b) a first-recombinant sequence-specific recombinase target site, wherein the 5' end of the first-recombinant sequence-specific recombinase target site is derived from the 5' end of the acceptor sequence-specific recombinase target site from the acceptor and the 3' end of the first-recombinant sequence-specific recombinase target site is derived from the 3' end of the first-donor sequence-specific recombinase target site of the donor construct; c) a unique restriction enzyme site or polylinker; d) the donor-partial selectable marker; e) a second-recombinant sequence-specific recombinase target site located within the recombinant-functional selectable marker gene and adjacent to the donor-partial selectable marker and the acceptor-partial selectable marker, wherein the 5' end of the second-recombinant sequence-specific recombinase target site is derived from the 5' end of the second-donor sequence-specific recombinase target site from the donor construct and the 3' end of the second-recombinant sequence-specific recombinase target site is derived from the 3' end of the acceptor sequence-specific recombinase target site of the acceptor construct; f) the acceptor-partial selectable marker, wherein the acceptor-partial selectable marker adjoins the donor-partial selectable marker to produce a newly-created recombinant-functional selectable marker; and, g) an origin of replication.

In a preferred embodiment, the final desired recombination product contains a gene or DNA sequence of interest inserted into the unique restriction enzyme site or polylinker such that the gene or DNA sequence of interest is under the control of the first promoter. In such an embodiment, the gene or DNA sequence of interest is joined to the 3' end of the first-recombinant sequence-specific recombinase target site such that a functional transcriptional unit is formed so that the gene or DNA sequence of interest is expressed as a protein driven by the first promoter of the acceptor construct. hi a more preferred embodiment, the gene of interest is joined to the 3' end of the first-recombinant sequence-specific recombinase target site such that a functional translational reading frame is created wherein the gene or DNA sequence of interest is expressed as a fusion protein with an affinity domain or tag sequence derived from the acceptor plasmid and under the expression control of the first promoter of the acceptor construct.

In another preferred embodiment, the final desired recombination construct further comprises an acceptor-functional selectable marker gene derived from the acceptor construct. If an acceptor-functional selectable marker gene is present in addition to the newly-created recombinant-functional selectable marker, the acceptor-functional selectable marker is a different selectable marker from the newly-created recombinant-functional selectable marker. The present invention should not be limited by the nature of the selectable marker genes chosen; the marker genes may result in positive or negative selection and may be chosen from the group including, but not limited to, the chloramphenicol resistance gene, the ampicillin resistance gene, the tetracycline resistance gene, the kanamycin resistance gene, the streptomycin resistance gene, the strA gene and the sacB gene.

Utility

The subject methods find use in a variety of different applications, where such applications are generally those protocols and methods in which the transfer of a nucleic acid of interest from one vector to another, e.g., the cloning of a nucleic acid from an initial vector into a final vector, is desired. As such, the subject methods are particularly suited for use in cloning nucleic acids of interest, including whole libraries, from an initial vector into an expression vector, where the expression vector may be functionalized to express the polypeptide or protein encoded by the nucleic acid of interest located on it in a variety of different desired environments and/or under desired conditions, e.g., in a cell of interest, in response to a particular stimulus, tagged by a detectable marker, etc.

As such, the expression vectors produced by the subject methods find use in a variety of different applications, including the study of polypeptide and protein function and behavior, i.e., in the characterization of a polypeptide or protein, either known or unknown; and the like. In the broadest sense, the subject methods find application in any method where traditional digestion and ligation protocols are employed to transfer or clone a nucleic acid from one vector to another, e.g., cloning digestion and ligation protocols, where the expression vectors produced by the subject methods find use in research applications, as well as other applications, e.g., protein production applications, therapeutic applications, and the like.

Systems

Also provided are systems for use in practicing the subject methods. The subject systems at least include a donor vector and an acceptor vector as described above. In addition, the subject systems may include a recombinase which recognizes the recombinase sites present on the donor and acceptor vectors. The systems may also include, where desired, a host cell, e.g., in in vivo methods of expression vector production, as described above. Other components of the subject systems include, but are not limited to: reaction buffer, controls, etc.

Libraries

Figure 2D:
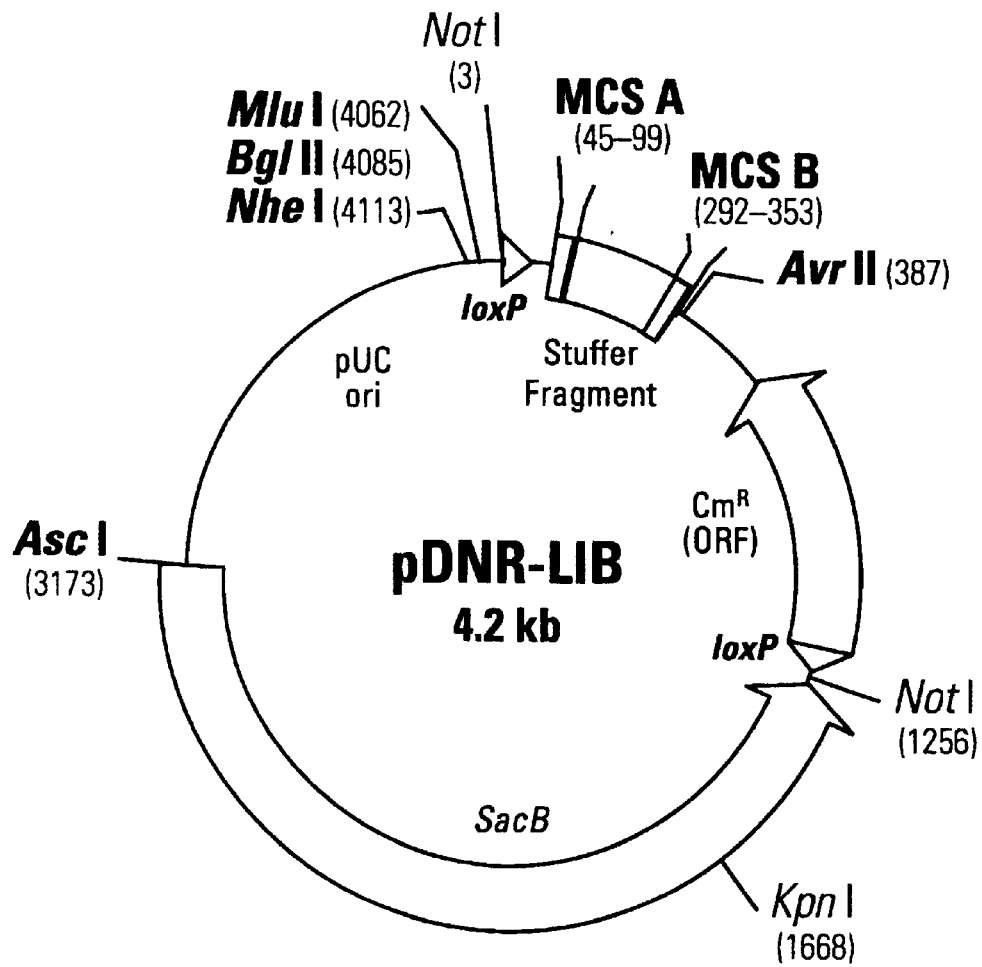

Also provided are nucleic acid libraries cloned into donor and/or acceptor vectors of the subject invention. These nucleic acid libraries are made up of a plurality of individual donor/acceptor vectors where each distinct constituent member of the library has a different nucleic acid portion or component, e.g., genomic fragment, cDNA, of an original whole nucleic acid library, i.e., fragmented genome, cDNA collection generated from the total or partial mRNA of an mRNA sample, etc. In other words, the libraries of the subject invention are nucleic acid libraries cloned into donor or acceptor vectors according to the subject invention, where the nucleic acid libraries include, but are not limited to, genomic libraries, cDNA libraries, etc. Specific donor/acceptor libraries of interest include, but are not limited to: Human Brain Poly A+RNA; Human Heart Poly A+RNA; Human Kidney Poly A+RNA; Human Liver Poly A+RNA; Human Lung Poly A+RNA; Human Pancreas Poly A+RNA; Human Placenta Poly A+RNA; Human Skeletal Muscle Poly A+RNA; Human Testis Poly A+RNA; Human Prostate Poly A+RNA and the like. With donor libraries according to the subject invention, the subject methods permit the rapid exchange of either individual clones of interest, groups of clones or potentially an entire cDNA library to a variety of expression vectors. The cDNA library is generated using a pDonor construct as the cloning vector (a pDonor library, e.g., pDNR-Lib as shown in FIG. 2D). The entire library may then be transferred (using either an in vitro or an in vivo recombination reaction) into any expression vector modified to contain an acceptor sequence-specific recombinase target site (e.g., a lox site) (i.e., an acceptor construct). This solves an existing problem in the art, in that there is no way, using existing vector systems, to exchange the inserts in a library made in one expression vector en masse (i.e., as an entire library) to a different expression vector.

Kits

Also provided are kits for use in practicing the subject methods. The subject kits at least include at least one donor vector and a recombinase that recognizes the recombinase sites of the donor vector. The subject kits may further include other components that find use in the subject methods, e.g., acceptor vectors; reaction buffers, positive controls, negative controls, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

Example 1

Construction of a pDonor Construct

This example describes a donor construct, the pD3 vector, which contained two loxP sites, a polylinker, a chloramphenicol resistance gene ($Cm^R$) open reading frame lacking a promoter, a standard origin of replication (derived from pUC19) and an ampicillin resistance gene ($Amp^R$) with its associated promoter. If a gene of interest is contained within pD3, any number of plasmid expression constructs containing this gene of interest can be constructed rapidly (e.g., within a single day). The expression constructs (the acceptor construct or the pAcceptor used in this example was pCM-VmycloxP (described below)) contained a sequence-specific recombinase target site, a promoter capable of expressing a gene of interest, an antibiotic resistance gene other than chloramphenicol (e.g., ampicillin), and a promoter positioned such that upon recombination of the pAcceptor with pD3, the promoter drove expression of the $Cm^R$ open reading frame from pD3.

Using a site-specific recombinase, Cre, a fragment of the initial donor construct encoding the gene of interest and the $Cm^R$ open reading frame recombined into the pAcceptor construct at its loxP site, resulting in the production of a vector in which the fragment of pD3 having the $Cm^R$ open reading frame was placed under the control of the second promoter on pCMVmycloxP. The recombination of pD3 and pCMVmycloxP to form the final desired recombinant construct was selected for by the ability of cells transformed with the constructs to grow in the presence of chloramphenicol.

The plasmid backbone used to generate pD3 was the pUC19 plasmid. Thus, the origin of replication and the second selectable marker gene of pD3 were the pUC origin of replication and the pUC Ampicillin resistance gene, respectively. This base vector further was derived to generate pD3 as follows:

1. pUC19 was digested with AatII and SapI to remove the region containing the LacZ gene and polylinker (nucleotides 2617–2686; 1–690). Into the remaining fragment were cloned two double-stranded oligonucleotides made by annealing the following two pairs of single stranded oligonucleotides:

L o x P 1 - u p :
   5'-CGCGGCCGCATAACTTCGTATAGCATACATT
   ATACGAAGTTATCAGTCGACG-3' (SEQ ID No. 1);

L o x P 1 - d o w n :
   5'-AATTCGTCGACTGATAACTTCGTATAATGTA
   TGCTATACGAAGTTATGCGGCCGCGACGT-3' (SEQ ID No. 2);

L o x P 2 - u p :
   5'-AATTCGGATCCATAACTTCGTATAGCATACA
   TTATACGAAGTTATGCGGCC-3' (SEQ ID No. 3);

L o x P 2 - d o w n :
   5'-AGCGGCCGCATAACTTCGTATAATGTATGCT
   ATACGAAGTTATGGATCCG-3' (SEQ ID No. 4).

The first pair of oligonucleotides encoded overhangs for AatII and EcoRI and the second pair encoded overhangs for EcoRI and SapI. These two pairs of oligos were thus ligated at their common EcoRI overhang and were subsequently able to be cloned into the AatII and SapI-digested pUC19 DNA. In the process, the SapI site was lost. In addition to the restriction sites mentioned, the LoxP1-up/down oligonucleotide pair also encoded a NotI site (GCGGCCGC) (SEQ ID No. 5). Similarly, the LoxP2-up/down pair also encoded a NotI site and a BamHI site (GGATCC) (SEQ ID No. 6). This first construct is called pD1.

2. pD1 was digested with BamHI and EcoRI, and a PCR fragment encoding the chloramphenicol resistance gene open reading frame ($Cm^R$) and termination sequence (nucleotides: 1932–1115, complement of the vector pProTet.E121, available from CLONTECH) was inserted using an EcoRI site and a BglII site engineered into the following reverse and forward PCR primers, respectively:

$Cm^R$ - f w d :
   5'-ATGCTTGATACTAGATCTTTCAGGAGCTAA
   GGAAGCTA-3' (SEQ ID No. 7);

$Cm^R$ - r e v :
   5'-ATGCTGAATTCTGGATCCTGGTCATGACTAG
   TGCTT GG-3' (SEQ ID No. 8).

This resulted in the placement of the $Cm^R$ open reading frame adjacent to the 5' end of the second loxP site but in the reverse 5' to 3' orientation. In addition, the original BamHI site in pD1 was destroyed and a new BamHI site was created adjacent to the EcoRI site. This vector is called pD2.

3. pD2 was cut with NotI and religated, so as to invert the orientation of the cassette encoding the LoxP sites and the $Cm^R$ open reading frame with respect to the ampicillin resistance selectable marker in the pUC19 backbone. This construct was called pD3.

4. pD3 is digested with EcoRI and BamHI and a PCR fragment encoding the T1 termination sequence (nucleotides 232–343 of pPROTet.E121) is inserted by standard methods. The resultant plasmid is pD4.

5. pD4 is restricted with EcoRI and BamHI and a PCR fragment encoding the SV40 polyadenylation sequence is cloned into the vector. The resultant vector is pD5.

6. PD5 is digested with BamHI and SalI and an oligo encoding a multiple cloning site is cloned into the BamHI and SalI sites to generate the final basic donor construct.

Example 2

Construction of pCMV-myc-LoxP

Acceptor constructs for the donor recombination system are generally expression vectors which have been modified by the insertion of a loxP or other sequence-specific recombinase target site and a prokaryotic promoter in a position 3' of the sequence-specific recombinase target site and oriented such as to direct transcription through the sequence-specific recombinase target site. It is also possible to utilize readthrough transcription from other promoters in the expression vector, provided that their orientation and distance from the loxP site is such that they can drive expression of the donor partial-selectable marker gene upon recombination of the acceptor vector with the desired fragment of the donor vector. The presence of a loxP site on the acceptor construct permitted the rapid subcloning or insertion of the gene interest contained within the pDonor vector to generate a final recombination construct capable of expressing the gene of interest. The acceptor construct may encode a protein domain such as an affinity domain or sequence tag including, but not limited to, glutathione-S-transferase (GST), maltose binding protein (MBP), protein A, protein L, a polyhistidine tract, the c-Myc Tag, the HA tag, the Flag Tag, Green Flourescence protein, etc. A variety of commercially-available expression vectors encoding such affinity domains and tag sequences are known in the art. When the acceptor construct encodes an affinity domain, a fusion protein comprising the affinity domain and the protein of interest is generated when the proper pDonor fragment and the acceptor constructs are recombined.

To generate final recombination constructs having the appropriate transcriptional fusions, a sequence-specific recombinase target site was placed after (i.e., downstream of) the start of transcription in the acceptor construct. In designing the oligonucleotide comprising the sequence-specific recombinase target site, care was taken to avoid introducing a start codon (the sequence "ATG") which might inappropriately initiate translation. Also, when generating a final recombination construct product having an appropriate translational fusion between the acceptor-encoded protein domain and the donor-encoded gene of interest, care was taken to place the loxP site in the correct reading frame such that an open reading frame was maintained through the sequence-specific recombinase target site on pAcceptor, and the reading frame in the sequence-specific recombinase site on pAcceptor was in-frame with the reading frame found in the first sequence-specific recombinase target site contained within the pDonor construct. In addition, the oligonucleotide comprising the sequence-specific recombinase target site on pAcceptor and the first sequence-specific recombinase target site contained within the donor were designed to avoid the introduction of in-frame stop codons. The gene of interest contained within the pDonor construct was cloned in a particular reading frame so as to facilitate the creation of the desired fusion protein.

Methods for modification of one expression vector are provided below to illustrate the creation of suitable pAcceptor constructs. The general strategy involves the generation of a linker containing a sequence-specific recombinase target site by annealing two complementary oligonucleotides. The annealed oligonucleotides form a linker having sticky ends which were compatible with ends generated by restriction enzymes whose sites are conveniently located in the parental expression vector (e.g., within the polylinker of the parental expression vector). In addition, but not necessarily, a prokaryotic promoter was cloned downstream of the sequence-specific recombinase target site with it's 5' to 3' orientation such that it directed expression through the sequence-specific recombinase target site. pCMV-myc-LoxP is an example pAcceptor construct. It was generated from pCMV-Myc (available from CLONTECH) in the following way:

1. pCMV-Myc was digested with SfiI and BglII.
2. A double-stranded oligonucleotide encoding an overhang at its 5' end compatible with SfiI; a LoxP site; and an overhang at its 3' end compatible with BglII was generated by annealling the following oligonucleotides together:

LoxPMyc-up:
5'-AGATAACTTCGTATAGCATACATTATACGAA GTTATA-3' (SEQ ID No. 09);

LoxPMyc-down:
5'-GATCTATAACTTCGTATAATGTATGCTATACG AAGTTATCTCCA-3' (SEQ ID No.10).

This oligonucleotide was then cloned into the digested pCMVMyc vector to generate pAccl.

3. The plasmid pAccl was then digested with BglII and NheI into which a PCR fragment encoding the ampicillin promoter from pUC19 (nucleotides: 2620–2500, complement) was cloned. This fragment was generated using appropriate primers encoding BamHI and NheI restriction sites as follows:

AmpProFwd:
5'-ATGCTGGATCCAATATTATTGAAGCATTTATCA GG-3' (SEQ ID No. 11);

AmpProRev:
5'-TCCATGCTGCTAGCACGTCAGGTGGCACTT TTCG-3' (SEQ ID No. 12).

The resultant plasmid is pCMVMycLoxP, which is a basic Acceptor plasmid having a LoxP site and adjacent promoter to drive expression of the gene of interest in the same 5' to 3' orientation as the LoxP site and a second promoter (acceptor partial selectable marker gene), oriented in the reverse 5' to 3' direction as the LoxP site and placed adjacent to the 3' end of said LoxP site.

A similar strategy to generate other types of acceptor vectors will be readily apparent to those skilled in the art. This strategy can be employed to generate any number of pAcceptor constructs. It is only necessary to design the oligos and PCR primers with appropriate restriction sites to match those in the polylinker of the construct to be adapted.

Example 3

Generation of 10 Additional Acceptor Vectors 10 additional acceptor vectors, as described in FIGS. 3A–3J have been made as follows. The construction of these vectors was as follows:

Each parental vector used to generate the various acceptors was cut with two restriction enzymes that cut within the MCS of the vector, as detailed below. Into these was inserted a PCR fragment of approx. 170 bp generated using various primers (described below) and pCMVMycLoxP, the acceptor molecule described above (see example 2 above) as a template. The primers are named either LoxP or AmpPro (to designate to which part of the template they are complementary) plus the name of the restriction enzyme present in the 5' end of the primer. These restriction sites match the ones cut in the MCS of the vector to be modified. The fragment generated in this PCR reaction encodes the LoxP site and the ampicillin promoter from the pCMVMycLoxP acceptor.

List of the 10 vectors used and restriction sites and primers used in the construction of each.

1. pGADT7: Cut with EcoRI and BamHI insert PCR fragment made with primers LoxP-EcoRI and AmpPro (cut with enzymes EcoRI and BamHI)
2. pGBKT7: Cut with EcoRI and BamHI insert PCR fragment made with primers LoxP-EcoRI and AmpPro (cut with enzymes EcoRI and BamHI)
3. pIRESneo: Cut with EcoRI and BamHI insert PCR fragment made with primers LoxP-EcoRI and AmpPro (cut with enzymes EcoRI and BamHI)
4. pEGFP-C1: Cut with HindIII and BamHI insert PCR fragment made with primers LoxP-HindIII and AmpPro-BamHI (cut with enzymes HindIII and BamHI)
5. pECFP-C1: Cut with HindIII and BamHI insert PCR fragment made with primers LoxP-HindIII and AmpPro-BamHI (cut with enzymes HindIII and BamHI)
6. pEYFP-C1: Cut with HindIII and BamHI insert PCR fragment made with primers LoxP-HindIII and AmpPro-BamHI (cut with enzymes HindIII and BamHI
7. pTRE2: Cut with SacII and BamHI insert PCR fragment made with primers LoxP-sacII and AmpPro-BamHI (cut with enzymes SacII and BamHI)
8. pRevTRE: Cut with HindIII and ClaI insert PCR fragment made with primers LoxP-HindIII and AmpPro-ClaI (cut with enzymes HindIII and ClaI)

9. pLNCX: Cut with HindIII and ClaI insert PCR fragment made with primers LoxP-HindIII and AmpPro-ClaI (cut with enzymes HindIII and ClaI 10. pIRES2-EGFP: Cut with EcoRI and BamHI insert PCR fragment made with primers LoxP-EcoRI and AmpPro-BamHI (cut with enzymes EcoRI and BamHI)

Primers for amplification of insert, providing various restriction enzyme ends (underlined) to enable cloning into above vectors.

1. LoxP-EcoRI

Sequence {5'-3'}: GATGCT GAATTCATAACTTCGTATAGCATACATTAT (SEQ ID NO:13) a 36 mer

MW-O: 11025 MW-N: 11587 TM: 66.91666 Extinction Coef: 399 Mass(ug) per OD: 29.0401

2. AmpPro-BHI

Sequence {5'-3'}: AGTCT GGATCCACGTCAGGTGGCACTTTTCG (SEQ ID NO: 14) a 31 mer

MW-O: 9512 MW-N: 9994 TM: 73.40323 Extinction Coef: 320 Mass(ug) per OD: 31.23125

3. LoxP-HindIII

Sequence {5'-3'}: ATGCT AAGCTTCGATAACTTCGTATAGCATACATTAT (SEQ ID NO:15) a 37 mer MW-O: 11314 MW-N: 11892 TM: 67.85135 Extinction Coef: 406 Mass(ug) per OD: 29.29064

4. AmpPro-ClaI

Sequence {5'-3'}: AGTCT ATCGATACGTCAGGTGGCACTTTTCG (SEQ ID NO:16) a 31 mer

MW-O: 9511 MW-N: 9993 TM: 71.20968 Extinction Coef: 325 Mass(ug) per OD: 30.74769

5. LoxP-NheI

Sequence {5'-3'}: TCCATGCT GCTAGCATAACTTCGTATAGCATACATTAT (SEQ ID NO:17) a 38 mer MW-O: 11579 MW-N: 12173 TM: 69.63158 Extinction Coef: 405 Mass(ug) per OD: 30.05679

6. LoxP-SacII

Sequence {5'-3'}: TAGTACTCCGCGGATAACTTCG-TATAGCATACATTAT (SEQ ID NO:18) a 37 mer MW-O: 11315 MW-N: 11893 TM: 69.68919 Extinction Coef: 401 Mass(ug) per OD: 29.65835

The primers were all made and PAGE purified by our regular supplier (Keystone labs) and were resuspended in water to a concentration of 100 pmol/ul in water.

Example 4

In Vitro Recombination Using the pDonor Recombination System

The pDonor recombination system permits in vitro recombination of two constructs. FIG. 1 provides schematic showing the strategy employed for in vitro recombination. pDNR-1,2,3 represent typical pDonor constructs which contains two loxP sites, a chloramphenicol resistance gene open reading frame which lacks a promoter, an origin of replication and an ampicillin resistance marker. The desired Acceptor vector shown contains a loxP site, a prokaryotic promoter in opposite orientation to the loxP site to drive the chloramphenicol open reading frame of pDNR-1,2,3, an ampicillin resistance gene, a eukaryotic or prokaryotic promoter or fusion tag to permit expression of the gene of interest under appropriate conditions, and a pUC origin of replication.

To achieve generation of the expression vector from the donor and acceptor, the following were mixed together on ice in a standard eppendorf microcentrifuge tube: 0.5 µg pCMVmycloxP (representing the Acceptor vector); 0.5 µg pD3 (representing the Donor vector); 2 µl 10×Cre reaction buffer (10×Cre reaction buffer contains: 500 mM Tris-HCl (pH 7.5) and 300 mM NaCl); 10 mM $MgCl_2$, 1 µl 20×BSA (20×BSA contains 2 mg/ml BSA (NEB)); 25 Units Cre recombinase (Novagen); $H_2O$ to 20 µl total.

Once the reagents were mixed, the reaction was incubated for 15 mins at 37° C. Following the reaction, the mixture was heated to 65° C. for 10 mins to inactivate the Cre enzyme. Finally, an aliquot of the reaction mix was transformed to E. coli using standard methods (e.g., electroporation), and the transformed bacteria selected on LB plates containing 60 µg/ml Chloramphenicol.

Alternatively, the pDonor vector may be incubated with Cre alone under the conditions described above; followed by purification of the fragment bearing the gene of interest, e.g., by gel electrophoresis, and subsequent recombination of the purified fragment into the pAcceptor vector, again according to the method above.

Example 5

The Use of Modified LoxP Sites to Increase Expression of the Protein of Interest The pDonor and pAcceptor constructs employed in the pDonor recombination system of the present invention are designed such that construct recombination results in the introduction of a loxP site between the promoter and the gene of interest. LoxP sites consist of two 13 bp inverted repeats separated by an 8 bp spacer region. Transcripts of the gene of interest produced from a pDonor-pAcceptor recombination construct comprising a loxP site have two 13 nucleotide perfect inverted repeats within the 5' untranslated region (UTR) and have the potential to form a stem-loop structure. In fact, this will occur in those cases where pAcceptor does not encode an affinity domain at the amino-terminus of the fusion protein. However, it is possible also to construct pDonor and pAcceptor constructs containing mutated loxP sequences. Mutated loxP sequences which comprise point mutations that create mismatches between the two 13 bp inverted repeat sequences within the loxP sites and have mismatches at different positions in the inverted repeats located within a loxP site may be used. The suitability of any pair of mutated lox sites for use in the pDonor recombination system may be tested by replacing the sequence-specific recombinase target sites in pDonor and pAcceptor with a site to be tested. The two modified vectors are then recombined in vitro as described in Example 3 and the recombination reaction mixture is used to transform E. coli cells. The transformed cells are then plated on selective medium (e.g., Cm plates) in order to determine the efficiency of recombination between the two mutated lox sites (Example 3). The efficiency of recombination between the two mutated lox sites is compared to the efficiency of recombination between two wild-type loxP sites. It will be apparent to those skilled in the art that a similar strategy can be employed for the modification of frt sites when the FLP recombinase is employed for the recombination event, or other such recombinase sites as might be used. The frt site, like lox sites, contains two 13 bp inverted repeats separated by an 8 bp spacer region.

Example 6

Alternative Conformations of pAcceptor and pDonor

The above-described constructs may be altered in the structural organization of their respective components, however, both constructs must be altered such that following recombination, the donor-partial and acceptor-partial selectable markers comprise an intact, recombinant-functional selectable marker, and additionally, the first promoter is operably linked to the gene or DNA sequences of interest. For example, the invention could be done in a similar fashion as described, except that the positions and orientations of the donor-partial selectable marker on the Donor construct and the acceptor-partial selectable marker on the Acceptor construct are switched. The final result of the recombination between the proper donor fragment (or first donor fragment) and the acceptor construct still generates a recombinant-functional selection marker. Likewise, vectors such that the selection marker comprises two fragments and forms a recombinant-functional selectable marker in the final product by reading through the second sequence-specific recombinase target site are also included within this invention.

Example 7

Generation of Multiple Expression Constructs for Luciferase in a Single Day

Using the Donor recombination system, it is possible to transfer one or many genes into multiple acceptor expression vectors at substantially the same time. To demonstrate this, the luciferase gene cloned into the multiple cloning site of pDNR-1, so generating pDNR-luc. The luciferase gene was then transferred from pDNR-luc into transferred to 10 different acceptor vectors simultaneosly using the method described in EXAMPLE 4. To do this, each of ten individual acceptor vectors, as detailed in FIGS. 3A to 3J, was placed in an eppendorf tube in reaction buffer as described in EXAMPLE 4. To each tube was then added 200 ng of pDNR-luc and 1 unit of cre recombinase. The reactions were incubated at 37° C. for 15 mins and then the Cre recombinase was inactivated by heating to 65° C. for 10 mins. Each reaction was then transformed individually into a separate aliquot of electro-competent DH5-alpha *E. coli*. These were allowed to grow for 1 hour in the absence of selection and then were plated out on selective agar plates containing 30 ug/ml chloramphenicol and 7% w/v sucrose. The following day, 3 colonies from each transformation were picked and grown-up for mini prep restriction digest analysis to determine if the desired recombinant had been made. Of the 30 clones analyzed in total (3 for each construct), 27 were correct, thus demonstrating that it is possible using the subject methods to readily generate multiple expression constructs—in this example 10 constructs—in a single day.

Example 8

Comparable Expression Levels for HEK 293 Cells Transfected Using Creator™ and Standard Vectors To compare the expression level achievable with Creator vectors (i.e., donor and acceptor vectors of the subject methods) to that generated using standard vectors, HEK 293 cells were transfected using the Calcium Phosphate method with either the pLP-EGFP-luc expression vector generated as part of example 7 above, or the comparable vector made using traditional cloning methods—pEGFP-Luc (available from CLONTECH). 24 hours after transfection, the level of fluorescence and the % of cells transfected was determined by both fluorescence microscopy and by FACS analysis. The result showed that while there is some reduction in expression associated with the Creator vectors, it is not a significant hindrance to adequate expression.

Example 9

Detection of Myc and Max Interaction by Yeast Two-hybrid Analysis

The interaction of myc and max proteins was tested by yeast two-hybrid interaction. To do this, relevant coding fragments of the human myc and max genes were first cloned in to pDNR-I by standard restriction cloning methods. These genes were then each transferred by use of the subject methods, as described in example 4 above, to both the pLP-GBKT7 (GAL4 DNA binding domain—bait vector) and the pLP-GADT7 (GAL4 activation domain—prey vector). AH109 yeast cells were then co-transformed with either pLP-GADT7 and pLP-GBKT7 alone, or with the same two expression vectors, but containing either myc or max. The yeast were then grown on selective medium lacking leucine and tryptophan in order to select for growth of yeast containing both constructs. The strength of the interaction between the protein expressed in the bait and the prey constructs was then determined using an alpha-galactosidase quantitative assay and normalized for culture density, as described in the MATCHMAKER system III user manual (available from CLONTECH). In this way, it was shown that myc and max interact well, but the homodimers do not.

Example 10

Inducible Expression of Luciferase in HeLa Cells Using pLP-TRE-Luc

The expression construct pLP-TRE-Luc generated by recombination of pLP-TRE and pDNR-Luc as described in Example 7 above, according to the method in example 4 above, was transfected into HeLa Tet-Off cells (available from CLONTECH) using the geneporter lipofection kit (available from Gene Therapy Systems). The cells were then cultured for 48 hrs in the presence of varying concentrations of doxycycline. The cells were then harvested and assayed for luciferase activity. The luciferase activity varied over several orders of magnitude from high level expression to background levels, dependent on the level of Doxycycline present in the growth medium.

Example 11

High Level Luciferase Induction with pLP-TRE-luc and pLP-RevTre-Luc Compared to pTRE-luc As described in example 8 above, the level of expression from Creator vectors can be somewhat reduced when directly compared to comparable expression vectors made using conventional cloning methods. It should be noted in this example that both basal and maximal levels of expression are reduced. It is thought likely that this reduction is due to inhibition of RNA translation due to hairpins caused by the palindromic lox sites. As shown above, this reduction seems to have no significantly detrimental effect on the functionality of any of the expression vectors tested. In this current example we further show that this reduction in expression may actually be beneficial in the case of inducible expression. This is because the decrease in expression caused by the lox sites seems to more greatly affect low-level expression than it does maximal expression. For this reason, when fold induction of tet inducible vectors (either plasmid-based or retro viral) is compared between standard vectors and creator vectors the fold induction seen is much greater in the case of the creator vectors. To demonstrate this, HeLa tet-off cells were transiently transfected with pTRE2-Luc or pLP-TRE2-luc, or stably infected with pRevTRE-luc. Cells were then grown for 48 hrs in the presence or absence of lug/ml doxycycline and then assayed for luciferase activity. Both pLP-TRE2-luc and pLP-RevTRE-Luc were observed to show greater fold induction than pTRE2-Luc.

Example 12

Construction of Other Acceptor Vectors

All of the following acceptor vectors are made simply by taking the parental vector and using PCR to insert a sequence encoding the loxP site and the ampicillin promoter, into the MCS of the vector. Note that this sequence is present in all of the 10 acceptor vectors described above and can be obtained from them by PCR.

1: pLP-Shuttle, an acceptor vector for transferring genes of interest into an adenoviral vector, is made by inserting the above sequence into the NheI site and KpnI site of the pShuttle vector (available from CLONTECH). This vector could itself be used, without a gene of interest to then transfer the loxP site and ampicillin promoter to adenoviral DNA, e.g., Adeno-X DNA (available from CLONTECH), so as to creator a adenovirus acceptor vector.

2: pLP-BacPAK9, an acceptor vector for transferring genes of interest into an baculoviral vector, is made by inserting the above sequence into the EcoRI site and BglII site of the pBacPAK9 vector (available from CLONTECH). This vector could itself be used, without a gene of interest to then transfer the loxP site and ampicillin promoter to baculoviral DNA, e.g., Baculo Gold DNA (available from Pharmingen), so as to creator a baculovirus acceptor vector.

3: pLP-CMV-Myc, an acceptor vector providing constitutive mammalian expression from the CMV promoter of myc epitope-tagged gene of interest, is made by inserting the above sequence into the SfiI site and BglII site of the pCMV-Myc vector (available from CLONTECH)

4: pLP-CMV-HA, an acceptor vector providing constitutive mammalian expression from the CMV promoter of HA epitope-tagged gene of interest, is made by inserting the above sequence into the SfiI site and BglII site of the pCMV-HA vector (available from CLONTECH)

5: pLP-PROTet-6x(HN), an acceptor vector providing Tet-inducible bacterial expression of a 6x(HN)-tagged gene of interest, is made by inserting the above sequence into the HindIII and ClaI sites of pPROTet.E133 (available from CLONTECH). Since this vector has chloramphenicol resistance, it should additionally be modified by changing the chloramphenicol to ampicillin resistance.

It is evident from the above results and discussion that the subject invention provides an efficient method to transfer a nucleic acid from a first vector to a second vector, where the subject methods do not employ digestion and ligation protocols. Advantages provided by the subject invention include: the ability to transfer or clone a nucleic acid of interest from a single donor into a variety of different expression vectors at substantially the same time and in a known orientation and reading frame; the ability to readily identify successful clones; the ability to transfer many different genes to one or more expression vectors simultaneously; no longer needing to sequence the junctions of the transferred fragment and the expression vector or to resequence the gene transferred and the like. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A donor vector comprising:
   first and second recombinase recognition sites oriented in the same direction and flanking a partial selectable marker, wherein said first and second recombinase recognition sites are able to recombine with each other.

2. The donor vector according to claim 1, wherein said partial selectable marker is a coding sequence.

3. The donor vector according to claim 2, wherein said coding sequence is a coding sequence selected from the following group of genes: the chloramphenicol resistance gene, the ampicillin resistance gene, the tetracycline resistance gene, the kanamycin resistance gene, the streptomycin resistance gene and the SacB gene.

4. The donor vector according to claim 1, wherein said recombinase recognition sites are selected from the group consisting of: lox sites, att sites, dif sites and frt sites.

5. The donor vector according to claim 4, wherein said recombinase recognition sites are lox sites.

6. The donor vector according to claim 1, wherein said donor vector further comprises a second functional selectable marker.

7. The donor vector according to claim 6, wherein said second functional selectable marker is selected from the following group of genes: the chloramphenicol resistance gene, the ampicillin resistance gene, the tetracycline resistance gene, the kanamycin resistance gene, the streptomycin resistance gene and the SacB gene.

8. The donor vector according to claim 1, wherein said donor vector further comprises a coding sequence for a protein of interest.

9. The donor vector according to claim 1, wherein said donor vector is a plasmid, cosmid, bac, yac or virus.

10. An acceptor vector comprising:
    a single recombinase recognition site located between a first promoter and a partial selectable marker, wherein said components are positioned such that, upon recombination of said acceptor vector with a donor vector that comprises a coding sequence for a protein of interest flanked by two recombinase recognition sites, an expression vector is produced that comprises an expression cassette made up of said first promoter and said coding sequence which flank a recombinase recognition site.

11. The acceptor vector according to claim 10, wherein said partial selectable marker is a second promoter.

12. The acceptor vector according to claim 11, wherein said second promoter is oriented in the opposite direction of said first promoter.

13. The acceptor vector according to claim 10, wherein said partial selectable maker is a coding sequence for a selectable marker gene.

14. The acceptor vector according to claim 10, wherein said recombinase recognition sites are selected from the group consisting of: lox sites, att sites, dif sites and frt sites.

15. The acceptor vector according to claim 14, wherein said recombinase recognition site is a lox site.

16. The acceptor vector according to claim 10, wherein said acceptor vector further comprises an origin of replication.

17. The acceptor vector according to claim 10, wherein said acceptor vector is a plasmid, cosmid, bac, yac or virus.

18. The acceptor vector according to claim 10, wherein said first promoter is operably linked to a tag encoding sequence.

19. An expression vector comprising:
    (a) first and second recombinase recognition sites oriented in the same direction, wherein said first and second recombinase recognition sites recombine with each other;
    (b) an expression cassette for a protein of interest divided into two sub-parts that flank said first recombinase recognition site; and
    (c) a functional marker divided into two sub-parts that flank said second recombinase recognition site.

20. The expression vector according to claim 19, wherein said recombinase recognition sites are selected from the group consisting of: lox sites, att sites, dif sites and frt sites.

21. The expression vector according to claim 20, wherein said recombinase recognition sites are lox sites.

22. The expression vector according to claim 19, wherein said two sub-parts of said expression cassette are a promoter and a coding sequence.

23. The expression vector according to claim 22, wherein said coding sequence of said expression cassette is flanked by said first and second recombinase recognition sites.

24. The expression vector according to claim 19, wherein said two sub-parts of said selectable marker are a promoter and a coding sequence of a selectable marker.

25. The expression vector according to claim 24, wherein said selectable marker is selected from the following group of genes: the chloramphenicol resistance gene, the ampicillin resistance gene, the tetracycline resistance gene, the kanamycin resistance gene, the streptomycin resistance gene and the SacB gene.

26. The expression vector according to claim 25, wherein said sub-parts of said expression cassette are a promoter and a coding sequence, and wherein said expression cassette promoter and said selectable marker promoter are oriented in opposite directions.

27. The expression vector according to claim 19, wherein said vector is a plasmid, cosmid, bac, yac or virus.

28. The expression vector according to claim 27, wherein said vector is a plasmid.

* * * * *

SEQUENCE LISTING

<160> NUMBER OF SEQ ID NOS: 21

<210> SEQ ID NO 1
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 1
cgcggccgca taacttcgta tagcatacat tatacgaagt tatcagtcga cg      52

<210> SEQ ID NO 2
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 2
aattcgtcga ctgataactt cgtataatgt atgctatacg aagttatgcg gccgcgacgt      60

<210> SEQ ID NO 3
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 3
aattcggatc cataacttcg tatagcatac attatacgaa gttatgcggc c        51

<210> SEQ ID NO 4
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 4
agcggccgca taacttcgta taatgtatgc tatacgaagt tatggatccg         50

<210> SEQ ID NO 5
<211> LENGTH: 8
<212> TYPE: DNA
<213> ORGANISM: Artificial Sequence
<220> FEATURE:
<223> OTHER INFORMATION: synthetic oligonucleotide

<400> SEQUENCE: 5 gcggccgc                                                        8

<210> SEQ ID NO 6
<211> LENGTH: 6
<212> TYPE: DNA
<213> ORGANISM: Artificial Sequence
<220> FEATURE:
<223> OTHER INFORMATION: restriciton site

<400> SEQUENCE: 6 ggatcc                                                          6

<210> SEQ ID NO 7
<211> LENGTH: 38
<212> TYPE: DNA
<213> ORGANISM: Artificial Sequence
<220> FEATURE:
<223> OTHER INFORMATION: pcr primer

<400> SEQUENCE: 7
atgcttgata ctagatcttt caggagctaa ggaagcta                      38

<210> SEQ ID NO 8
<211> LENGTH: 38
<212> TYPE: DNA
<213> ORGANISM: Artificial Sequence
<220> FEATURE:
<223> OTHER INFORMATION: pcr primer

<400> SEQUENCE: 8
atgctgaatt ctggatcctg gtcatgacta gtgcttgg                      38

<210> SEQ ID NO 9
<211> LENGTH: 37
<212> TYPE: DNA
<213> ORGANISM: Artificial Sequence
<220> FEATURE:

```
<223> OTHER INFORMATION: oligonucleotide

<400> SEQUENCE: 9
agataacttc gtatagcata cattatacga agttata                              37

<210> SEQ ID NO 10
<211> LENGTH: 44
<212> TYPE: DNA
<213> ORGANISM: Artificial Sequence
<220> FEATURE:
<223> OTHER INFORMATION: oligonucleotide

<400> SEQUENCE: 10
gatctataac ttcgtataat gtatgctata cgaagttatc tcca                      44

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
atgctggatc caatattatt gaagcattta tca                                  33

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
tccatgctgc tagcacgtca ggtggcactt ttcg                                 34

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
gatgctgaat tcataacttc gtatagcata cattat                               36

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
agtctggatc cacgtcaggt ggcacttttc g                                    31

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
atgctaagct tcgataactt cgtatagcat acattat                              37
```

<210> SEQ ID NO 16
<211> LENGTH: 31
<212> TYPE: DNA
<213> ORGANISM: Artificial Sequence
<220> FEATURE:
<223> OTHER INFORMATION: primer

<400> SEQUENCE: 16
agtctatcga tacgtcaggt ggcacttttc g                          31

<210> SEQ ID NO 17
<211> LENGTH: 38
<212> TYPE: DNA
<213> ORGANISM: Artificial Sequence
<220> FEATURE:
<223> OTHER INFORMATION: primer

<400> SEQUENCE: 17
tccatgctgc tagcataact tcgtatagca tacattat                   38

<210> SEQ ID NO 18
<211> LENGTH: 37
<212> TYPE: DNA
<213> ORGANISM: Artificial Sequence
<220> FEATURE:
<223> OTHER INFORMATION: primer

<400> SEQUENCE: 18
tagtactccg cggataactt cgtatagcat acattat                    37

<210> SEQ ID NO 19
<211> LENGTH: 105
<212> TYPE: DNA
<213> ORGANISM: Artificial Sequence
<220> FEATURE:
<223> OTHER INFORMATION: Synthetic Vector

<400> SEQUENCE: 19
ttatcagtcg acggtaccgg acatatgccc gggaattcct gcaggatccg ctcgagaagc    60
tttctagacc attcgtttgg cgcgcgggcc cagtaggtaa gtgaa                   105

<210> SEQ ID NO 20
<211> LENGTH: 105
<212> TYPE: DNA
<213> ORGANISM: Artificial Sequence
<220> FEATURE:
<223> OTHER INFORMATION: Synthetic Vector

<400> SEQUENCE: 20
ttatcagtcg actggtacca gacatatgcc cgggaattcc tgcaggatcc gctcgagaag    60
ctttctagac cattcgtttg gcgcgcgcat gcagtaggta agtga                   105

<210> SEQ ID NO 21
<211> LENGTH: 101
<212> TYPE: DNA
<213> ORGANISM: Artificial Sequence
<220> FEATURE:
<223> OTHER INFORMATION: Synthetic Vector

<400> SEQUENCE: 21
ttatcagtcg actcggtacc gagcatatgc ccgggaattc ctgcaggatc cgctcgaaag    60
cttatctaga cattcgtttg gcgcgcatgc atagtaggta a                       101